US007780981B2

(12) United States Patent
DiPierro et al.

(10) Patent No.: US 7,780,981 B2
(45) Date of Patent: Aug. 24, 2010

(54) BIOSYNCHRONOUS TRANSDERMAL DRUG DELIVERY

(75) Inventors: Guy DiPierro, Hamilton, NJ (US); Steven A. Giannos, Quincy, MA (US)

(73) Assignee: Chrono Therapeutics, Inc., Hamilton, NJ (US)

( * ) Notice: Subject to any disclaimer, the term of this patent is extended or adjusted under 35 U.S.C. 154(b) by 778 days.

(21) Appl. No.: 11/162,525

(22) Filed: Sep. 13, 2005

(65) Prior Publication Data

US 2006/0062838 A1 Mar. 23, 2006

Related U.S. Application Data

(60) Provisional application No. 60/609,418, filed on Sep. 13, 2004.

(51) Int. Cl.
*A61K 9/70* (2006.01)
*A61N 1/30* (2006.01)

(52) U.S. Cl. ........................................ 424/449; 604/20

(58) Field of Classification Search .................. 424/449
See application file for complete search history.

(56) References Cited

U.S. PATENT DOCUMENTS

| | | | | |
|---|---|---|---|---|
| 4,379,454 | A | | 4/1983 | Campbell et al. |
| 4,708,716 | A | | 11/1987 | Sibalis |
| 4,917,895 | A | | 4/1990 | Lee et al. |
| 5,242,941 | A | | 9/1993 | Lewy et al. |
| 5,273,756 | A | | 12/1993 | Fallon et al. |
| 5,370,635 | A | | 12/1994 | Strausak et al. |
| 5,405,614 | A | | 4/1995 | D'Angelo et al. |
| 5,538,503 | A | * | 7/1996 | Henley ........................ 604/20 |
| 5,785,688 | A | | 7/1998 | Joshi et al. |
| 5,879,322 | A | | 3/1999 | Lattin et al. |
| 5,932,240 | A | | 8/1999 | D'Angelo et al. |
| 5,993,435 | A | | 11/1999 | Haak et al. |
| 6,068,853 | A | * | 5/2000 | Giannos et al. ............. 424/449 |
| 6,090,404 | A | | 7/2000 | Meconi et al. |
| 6,129,702 | A | | 10/2000 | Woias et al. |
| 6,165,155 | A | | 12/2000 | Jacobsen et al. |
| 6,211,296 | B1 | | 4/2001 | Frate et al. |
| 6,374,136 | B1 | | 4/2002 | Murdock |
| 6,595,956 | B1 | | 7/2003 | Gross et al. |
| 6,723,077 | B2 | | 4/2004 | Pickup et al. |
| 2003/0065294 | A1 | * | 4/2003 | Pickup et al. ............... 604/304 |
| 2007/0191815 | A1 | * | 8/2007 | DiPierro .................. 604/890.1 |

FOREIGN PATENT DOCUMENTS

| | | | |
|---|---|---|---|
| CA | 2142871 | | 3/1994 |
| JP | 2208813 | | 8/1990 |
| WO | PCT/GB02/04064 | | 3/2003 |
| WO | WO 2005/039685 | * | 5/2005 |

OTHER PUBLICATIONS

U.S. Appl. No. 11/162,517, filed Aug. 2007, DiPierro, Guy.*
R. Guy, "Current Status and Future Prospects of Transdermal Drug Delivery" Pharmaceutical Research, 1996, 13(12), pp. 1765-1769.*
V. Kotwal, "Enhancement of Iontophoretic Transport of Diphenhydramine Hydrochloride Thermosensitive Gel by Optimization of pH, Polymer Concentration, Electrode Design, and Pulse Rate" AAPS PharmSciTech, 2007, 8(4), E1-E6.*
L. Molander et al., "Reduction of tobacco withdrawl symptoms with a sublingual nicotine tablet: a placebo controlled study" Nicotine & Tob. Res., 2000, 2, pp. 187-191.*
S. Shin et al., "Enhanced bioavailability of triprolidine from the transdermal TPX matrix system in rabbits" Int. J. Pharm., 2002, 234, pp. 67-73.*
Shin et al., "Enhanced bioavailability of triprolidine from the transdermal TPX matrix system in rabbits", Int. J. Pharm., 2002, 234, pp. 67-73.*
Molander et al., "Reduction of tobacco withdrawl symptoms with a sublingual tablet: a placebo controlled study", Nicotine & Tob. Res., 2000, 2, pp. 187-191.*
International Search Report—PCT/US05/32672 (Jun. 14, 2006).
Lamberg, Lynn, "Chronotherapeutics: Implications for Drug Therapy," American Pharmacy, N831(11), pp. 20-23 (1991).
The Science and Practice of Pharmacy, 19$^{th}$ Ed., p. 1583, (1995).
Office Action from related U.S. Appl. No. 11/981,672 dated Mar. 23, 2009.
Office Action cited by the Examiner in related U.S. Appl. No. 11/083,178, dated Oct. 2, 2009.
Office Action cited by the Examiner in related U.S. Appl. No. 11/083,178, dated Oct. 29, 2008.
Office Action cited by the Examiner in related U.S. Appl. No. 11/981,672, dated Oct. 7, 2009.
Office Action cited by the Examiner in related U.S. Appl. No. 11/162,517, dated Nov. 24, 2009.
Office Action cited by the Examiner in related U.S. Appl. No. 10/711,389, dated Jul. 1, 2009.
Prosise et al., "Effects of Abstinence from Smoking on Sleep and Daytime Sleepiness," *Chest*, vol. 105, pp. 1136-1141 (1994).

* cited by examiner

*Primary Examiner*—Frederick Krass
*Assistant Examiner*—Brian Gulledge
(74) *Attorney, Agent, or Firm*—Foley & Lardner LLP

(57) ABSTRACT

Systems and methods for treating diseases, addictions and disorders in humans and animals involving synchronizing and tailoring the administration of drug compounds with the body's natural circadian rhythms, in order to counteract symptoms when they are likely to be at their worst. Automated and pre programmable transdermal drug administration system are used. This system can also utilize a pump or pressurized reservoir, and/or a system for removing depleted carrier solution, or other modulated dispensing actuator, in conjunction with micro-fabricated structures commonly referred to as Micro-needles, or heat, or iontophoresis, sonophoresis, or a wide range of chemical permeation enhancers.

18 Claims, 22 Drawing Sheets

BIOSYNCHRONOUS TRANSDERMAL DRUG DELIVERY

This application claims the benefit of U.S. Provisional Application No. 60/609,418 filed on Sep. 13, 2004 which is incorporated herein by reference. This application also relates to the subject matter of PCT application No. PCT/IB2004/002947 entitled Transdermal Drug Delivery Method and System filed on Sep. 13, 2004 which is incorporated herein by reference.

FIELD OF THE INVENTION

This invention relates, in general, to controlled drug delivery methods and systems, and, more specifically, to systems and methods for biosynchronous transdermal drug delivery. The invention further relates to the field of chronobiology in that the invention systems can be designed to modulate active agent delivery in accordance with biological rhythms. Drugs, pharmaceuticals, and other bioactive substances are delivered transdermally into a body in a manner that is synchronized with biological processes and/or biological rhythms so as to improve performance of the substance in the body. The invention also relates to overcoming active agent tolerance, which may be experienced from continuous administration, improve patient compliance, and in some cases reducing the amount of drug needed per dose due to advantages of biosynchronization.

RELEVANT BACKGROUND

In the field of drug delivery, it is recognized that supplying the drug in a correct temporal pattern is an important attribute of any drug delivery methodology. Controlled release drug delivery systems are intended to improve the response to a drug and/or lessen side effects of a drug. The recurring interest in chronopharmacology demonstrates the fact that biological rhythms are an important aspect of clinical pharmacology and should be taken into account when evaluating drug delivery systems (Hrushesky, W., J. Cont. Rel. 19:363 (1992), Lemmer, B., Adv. Drug Del. Rev. 6:19 (1991), Youn, C. B. J. Cont. Rel. 98 (3) 337 (2004) and Youn, C. B. J., Ed., "Chronopharmaceutics," John Wiley & Sons, New York (In preparation)).

The onset and symptoms of diseases such as asthma attacks, coronary infarction, angina pectoris, stroke and ventricular tachycardia are circadian phase dependent. In humans, variations during the 24 h day in pharmacokinetics (chrono-pharmacokinetics) have been shown for cardiovascular active drugs (propranolol, nifedipine, verapamil, enalapril, isosorbide 5-mononitrate and digoxin), anti-asthmatics (theophylline and terbutaline), anticancer drugs, psychotropics, analgesics, local anesthetics and antibiotics, to mention but a few. Even more drugs have been shown to display significant variations in their effects throughout the day (chronopharmacodynamics and chronotoxicology) even after chronic application or constant infusion (Ohdo, S. Drug Safety 26 (14) 999-1010 (2003)). Moreover, there is clear evidence that dose/concentration-response relationships can be significantly modified based on the time of day. Thus, circadian time has to be taken into account as an important variable influencing a drug's pharmacokinetics and its effects or side-effects (Bruguerolle, B., Clin. Pharmacokinet. Aug. 35 (2) 83-94 (1998)).

Studies indicate that the onset of certain diseases show strong circadian temporal dependency. This has led to the need for timed patterning of drug delivery as opposed to constant drug release (Lemmer B., Ciba Found Symp. 183: 235-47; discussion 247-53 (1995).

The term "controlled release" refers generally to delivery mechanisms that make an active ingredient available to the biological system of a host in a manner that supplies the drug according to a desired temporal pattern. Controlled release drug delivery systems may be implemented using: a) instantaneous release systems; b) delayed release systems, and c) sustained release systems. In most cases, controlled release systems are designed to maintain a sustained plasma level of an active ingredient in a drug within a human or animal host over a period of time.

Instantaneous release refers to systems that make the active ingredient available immediately after administration to the biosystem of the host. Instantaneous release systems include continuous or pulsed intravenous infusion or injections. Such systems provide a great deal of control because administration can be both instantaneously started and stopped and the delivery rate can be controlled with great precision. However, the administration is undesirably invasive as they involve administration via a puncture needle or catheter.

Delayed release refers to systems in which the active ingredient made available to the host at some time after administration. Such systems include oral as well as injectable drugs in which the active ingredient is coated or en-capsulated with a substance that dissolves at a known rate so as to release the active ingredient after the delay. Unfortunately, it is often difficult to control the degradation of the coating or encapsulant after administration and the actual performance will vary from patient to patient.

Sustained Release generally refers to release of active ingredient such that the level of active ingredient available to the host is maintained at some level over a period of time. Like delayed release systems, sustained release systems are difficult to control and exhibit variability from patient to patient. Due to the adsorption through the gastrointestinal tract, drug concentrations rise quickly in the body when taking a pill, but the decrease is dependent on excretion and metabolism, which cannot be controlled. In addition, the adsorption through the gastrointestinal tract in many cases leads to considerable side effects (such as ulcers), and can severely damage the liver.

Transdermal therapeutic systems (TTS) have been developed primarily for sustained release of drugs in situations where oral sustained release systems are inadequate. In some cases, drugs cannot be effectively administered orally because the active ingredients are destroyed or altered by the gastrointestinal system. In other cases the drug may be physically or chemically incompatible with the coatings and/or chelating agents used to implement sustained release. In other cases a transdermal delivery system may provide sustained release over a period of days or weeks whereas orally administered drugs may offer sustained performance over only a few hours. A wide variety of active substances can be delivered through transdermal systems so long as the active substance can be provided in a form that can cross the skin barrier, see for example, U.S. Pat. No. 6,638,528, which is incorporated herein by reference.

In most cases transdermal delivery systems are passive, taking the form of a patch that is attached to the skin by an adhesive. The TTS includes a quantity of the active substance, along with a suitable carrier if need be, in a reservoir, matrix or in the adhesive itself. Once applied, the active ingredient diffuses through the skin at a rate determined by the concentration of the active substance and the diffusivity of the active substance. However, a variety of physical and chemical processes at the skin/patch boundary affect the delivery rate and may eventually inhibit drug delivery altogether.

The original performance target for controlled drug delivery is to achieve a zero-order release rate of the drug, so that a constant efficacious drug concentration is maintained in the blood plasma. However, more than two decades of research in chronobiology and chronopharmacology have demonstrated the importance of biological rhythms to the dosing of medications as well as determine the influence of a patient's circadian or other biological rhythms on drug efficacy and efficiency. This research reveals that certain disease symptoms follow a daily pattern, with peak symptoms at certain times of the day. It has been widely acknowledged that hormones, neurotransmitters and other intra-body compounds are released in different amounts at different times of the day pursuant to daily patterns.

The new approach stems from a growing body of research that demonstrates that certain diseases tend to get worse at certain times of the day. By synchronizing medications with a patient's body clock, many physicians believe that the drugs will work more effectively and with fewer side effects. In some cases, the improvements have been so pronounced that doctors have been able to reduce dosages. Circadian physiologic processes have been found to alter drug absorption, distribution, metabolism, and excretion. As a result, drug doses need to be adjusted to meet the differing needs of target organs or tissues at various times of the day (see, L. Lamberg, American Pharmacy, N831 (11): 20-23 (1991)).

The continued interest in chronopharmacology shows the ever-increasing need to develop technologies to control the temporal profile in drug delivery. Research findings suggest that the onset and severity of many diseases are cyclic in nature, or follow circadian patterns. Drug tolerance adds to the need for modulation of drug dosing profiles. Additionally, skin irritation and sensitization caused by medications may require intervals during which no drug is administered. Therefore, this improved form of drug delivery will be very important to people who need medicine easily, painlessly and automatically delivered to their bodies in timed increments (see Smolensk, M. H. & Lamberg, L. *Body Clock Guide to Better Health: How to Use Your Body's Natural Clock to Fight Illness and Achieve Maximum Health*, Henry Holt & Company, New York (2001) and Grimes, J. et al., *J Pharmacol Exp Ther* 285 (2): 457-463 (1998)).

Active transdermal delivery systems have been developed to help regulate the delivery rate by providing mechanisms to improve drug delivery over time by "pumping" the active ingredient. One such system, (U.S. Pat. No. 5,370,635), describes a system for delivering a medicament and dispensing it to an organism for a relatively long period of time, for example at least a few days. The device can be adapted for positioning on the surface of the skin of a human or possibly an animal body in order to apply a medicament thereto from the outer side thereof. Conventional transdermal systems circumvent the disadvantages of the adsorption through the gastrointestinal tract, but they do not optimize or tailor the dosing regiment to offset peak symptoms. In addition the constant transdermal delivery of a drug can lead to severe side effects, including debilitating sleep disorders and ever increasing tolerance.

A simple type of transdermal chronotherapy is a biphasic profile, in which the drug concentration changes from a high to a low level (or vice versa) over time. Although the system can be physically applied or removed to alter the drug level, patient compliance with this procedure may be difficult, particularly during inconvenient hours. To generate a biphasic profile, the delivery system may utilize an external regulator, as described in Fallon et al. (U.S. Pat. No. 5,352,456, 1994) which illustrates a device for drug administration through intact skin that provides an initial pulse in the flux of the drug through the skin followed by a substantially lower flux of drug through the skin. Additionally, Fallon et al. (U.S. Pat. No. 5,820,875, 1998) later describe a device for the administration of a drug through an area of intact skin over a period of time in which the flux of the drug through the skin varies temporally in a controlled manner. The device is such that the skin flux of the drug varies in a controlled manner over the period of administration, typically from a high flux in the initial stage of administration to a lower flux in the later stage of administration.

Transdermal temporally controlled drug delivery systems, proposed by Giannos et al. (U.S. Pat. No. 6,068,853, 2000) coupled pH oscillators with membrane diffusion in order to generate a periodic release of a drug or active ingredient transdermally, without external power sources and/or electronic controllers. The intent was to address chronotherapy with a pulsatile transdermal system. The strategy was based on the observation that a drug may be rendered charged or uncharged relative to its $pK_a$ value. Since only the uncharged form of a drug can permeate across lipophilic membranes, including the skin, a periodic delivery profile may be obtained by oscillating the pH of the drug solution (see Giannos, S. A., "Pulsatile Delivery of Drugs and Topical Actives," in "Novel Topical Actives and Delivery Systems: Cosmetics, Dermatologicals and Transdermals", Edited by John. J. Wille, Jr.: Blackwell Publishing, Oxford UK (In press)).

Recently, an orally administered drug for arthritis treatment has suggested a chronotherapeutic approach using a delay release system. The delay is scheduled to release the active ingredient at the beginning of an interleukin 6 cascade that is believed to cause early morning stiffness in rheumatoid arthritis patients. By attempting to synchronize the drug delivery with a biological cycle it is believed that low doses may be used to achieve desired results. However, this system does not overcome the limitations of delayed release systems described above.

Although it is possible to meet the requirements of chronopharmacology with pills, this requires an enormous amount of discipline by the patient to comply with the treatment regiment, see for example, U.S. Pat. No. 6,214,379, which is incorporated herein by reference. As illustrated earlier, to achieve optimal results, many patients may need to wake up during the night to take their medication. Hence, what is needed is a non-invasive, reliable means of delivering drugs compounds in precisely timed and measured doses-without the inconvenience and hazard of injection, yet with improved performance as compared to orally delivered drugs.

Addressing patient compliance (taking the proper dosages at the prescribed times) is another critical problem facing caregivers and pharmaceutical firms alike. Studies show that only about half of patients take medications at the times and in the dosages directed by their physician. It is reported that each year, 125,000 deaths and up to 20% of all hospital and nursing home admissions result from patient noncompliance. It is estimated that non-compliance results in additional healthcare costs in excess of $100 billion per year in United States. These figures are even more pronounced for the elderly.

An individual's failure to comply with a dosing regimen, e.g. failure to take one or more doses of a drug or taking too many doses, will have an adverse impact upon the success of the regimen. Individuals may fail to comply with their drug dosing regimen for a number of reasons. For example, drug dosing regimens, such as every 4 hours, i.e., 8-12-4-8 involve a rigid dosing schedule that may be incompatible with an individual's personal schedule. Such a rigid dosing schedule when combined with normal human traits such as forgetfulness or denial of a medical condition, as well as a busy life, represent substantial obstacles to compliance with a drug dosing regimen. Accordingly, such rigid dosing regimens often result in the failure by an individual to take one or more doses at the prescribed time. This has an adverse impact on the levels of the therapeutic substance at the active site and consequently on the overall efficacy of the therapeutic substance. Hence, a need exists for systems and methods that increase patient compliance for administration of a variety of drugs.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

SUMMARY OF THE INVENTION

The present invention describes methods for treating diseases, addictions and disorders in humans. These methods involve synchronizing and tailoring the administration of drug compounds with the body's natural circadian rhythms, in order to counteract symptoms when they are likely to be at their worst, and are accomplished by using an automated and pre programmable transdermal drug administration system. This system can also utilize a pump or pressurized reservoir, and/or a system for removing depleted carrier solution, or other modulated dispensing actuator, in conjunction with micro-fabricated structures commonly referred to as Micro-needles, or heat, or iontophoresis, sonophoresis, (together referred to as the Mechanical Permeation Enhancers) or a wide range of chemical permeation enhancers.

More specifically, these methods synchronize and tailor drug administration to the human body's circadian rhythms to deliver varying dosages at varying times. This ensures that peak drug concentrations are present in the bloodstream to offset peak disease and addiction symptoms arising from variances and fluctuation in the body's natural circadian rhythms. Further, these methods ensure that less of a drug is in the bloodstream when disease and addiction symptoms are at there lowest. This minimizes negative side effects, and increases efficacy of the dosing regimen.

DETAILED DESCRIPTION OF THE PREFERRED EMBODIMENTS

Figure 1:
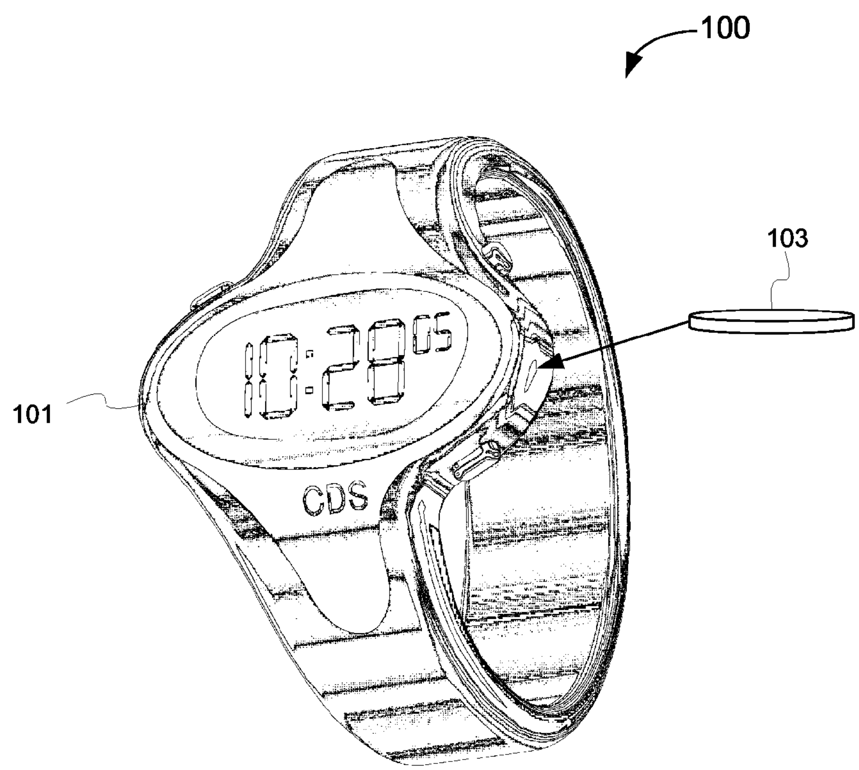
FIG. 1 shows an exemplary device useful for implementing the present invention.

Biological rhythms are periodic fluctuations in biological characteristics over time, which also include circadian as well as seasonal variations. The reality of circadian rhythms in animals including humans is well known (Halberg et al. J. Exp. Ther. Oncol. 3 (5) 223-260 (2003), Redfern et al. Chronobiology International 11 (4) 253-265 (1994)).

Circadian (approximately 24-hour) rhythms include the production of biological molecules such as endorphins, gonadotropin releasing hormone (GnRH), cortisol and adrenaline. These regulate the body's temperature and heart rate, changes in characteristics of blood, such as stickiness, and behaviors such as wakefulness, sleep and periods of activity.

Some of the rhythms that affect our bodies include:

- ultradian, which are cycles shorter than a day (for example, the milliseconds it takes for a neuron to fire, or a 90-minute sleep cycle)

circadian, which last about 24 hours (such as sleeping and waking patterns)

infradian, referring to cycles longer than 24 hours (for example monthly menstruation)

seasonal, such as seasonal affective disorder (SAD), which causes depression in susceptible people during the short days of winter.

Research demonstrates that certain disease symptoms follow a daily pattern, with peak symptoms at certain times of the day. It has been widely acknowledged that hormones, neurotransmitters and other intra-body compounds are released in different amounts at different times of the day pursuant to daily patterns. It is believed that the failure of current transdermal systems to synchronize drug administration with the body's natural rhythms often lead to (i) severe side effects, including debilitating sleep disorders (in the context of night-time nicotine administration, for example), (ii) ever increasing tolerance (in the case of nitroglycerin and other pharmaceuticals for example), (iii) more expensive therapies, due to the fact that more of a compound is needed because the daily body rhythm is ignored and time based dosing is not implemented.

In addition, many addictions follow a daily pattern consistent with one's circadian rhythms. For example, according to studies performed, immediately upon waking, smokers have peak nicotine cravings. These peak cravings return after each meal, due to the interplay of serotonin release as a trained response to the culmination of a meal. Our methods precisely time the administration of drugs so that they reach peak levels when symptoms are likely to be at their worst, and efficacy is greatly improved.

The present invention involves precisely timing the administration of drugs so that they reach peak levels in synchronization with times when symptoms are likely to be at their worst, or times at which the drugs are believed to be more effective in the body and/or better tolerated by the patient. The present invention is described in terms of a particular example of a drug delivery system that provides automated and precise control over dosing, with single-dose capability, (once while people sleep) or capability to administer separate and varying-sized doses many times throughout a multiple day period. The present invention also relates to the administration of different, distinct, drugs and dosages at different times of the day. The particular implementation is consistent with a commercial development of a miniaturized, automated and programmable non-invasive drug delivery system called the ChronoDose™ system being developed by the assignee of the present invention. The system enables controlling of the amount of drug exposed to the skin in a controlled time dependent way according to a programmed administration schedule that implements a desired dosage profile. In this manner the present invention enables one to precisely control and vary the time of drug release and the amount of each dose, pursuant to an easily set pre-programmed dosage profile. Research demonstrates that for certain symptoms, conditions and diseases, drug effects can be optimized when administered in a defined (and often varying) dosage at predefined times. This is known as Chronopharmacology (Reinberg, A. E., Concepts of Circadian Chronopharmacology, In "Temporal Control of Drug Delivery" edited by Hrushesky, W. J. M., Langer, R. S. and Theeuwes, F. Annal NY Academy of Science, New York. Volume 618 102-115 (1991), Lemmer, B. Pharmacol Res. 33(2) 107-15 (1996)).

To illustrate the importance of Chronopharmacology consider the following facts:

Asthma attacks are 100 times more likely between 4:00 and 6:00 AM.

Heart attacks and strokes are most likely to occur around 6:00 AM.

Variant Angina attacks occur 30 times more often in the middle of the night between 2:00 AM and 4:00 AM.

Smokers experience the highest cravings immediately upon waking up.

Lethargy and difficulty getting out of bed is highest immediately upon waking up early in the morning.

Cold and flu symptoms peak during nighttime and early morning hours, when cold medications are wearing off.

In accordance with the present invention, substances with proven or suspected chrono-pharmacological efficiency are integrated into a miniaturized, automated, programmable watch-like device, such as device (100) shown in FIG. 1. The delivery system (100) shown in FIG. 1 can be used for a variety of active compositions, and is small, fully automated and programmable. This system consists of a reusable wristwatch-like device (101) to control the time and dosage of drug delivery; and a small, disposable, 'reservoir' (103), which is about the size of a quarter or ½ dollar coin in a particular example, or is cylindrical in shape, that the user can simply pop-in to place on the watch-like platform. This reservoir lasts, for example, up to 72 hours, depending on the application. Shorter and longer reservoir lifetimes are contemplated. The device is readily adapted to be worn on the forearm, ankle, or other convenient body location.

In a particular application the replaceable reservoir can include a description of an administration schedule that can be used to manually or automatically program device (100) with an administration schedule. For example, a written schedule can be printed on or affixed to the reservoir (101) or electrically programmed using volatile or non-volatile memory. In this manner, a dosing profile can be prescribed and filled by a pharmacy in much the same manner as a conventional drug prescription is handled today.

Figure 3:
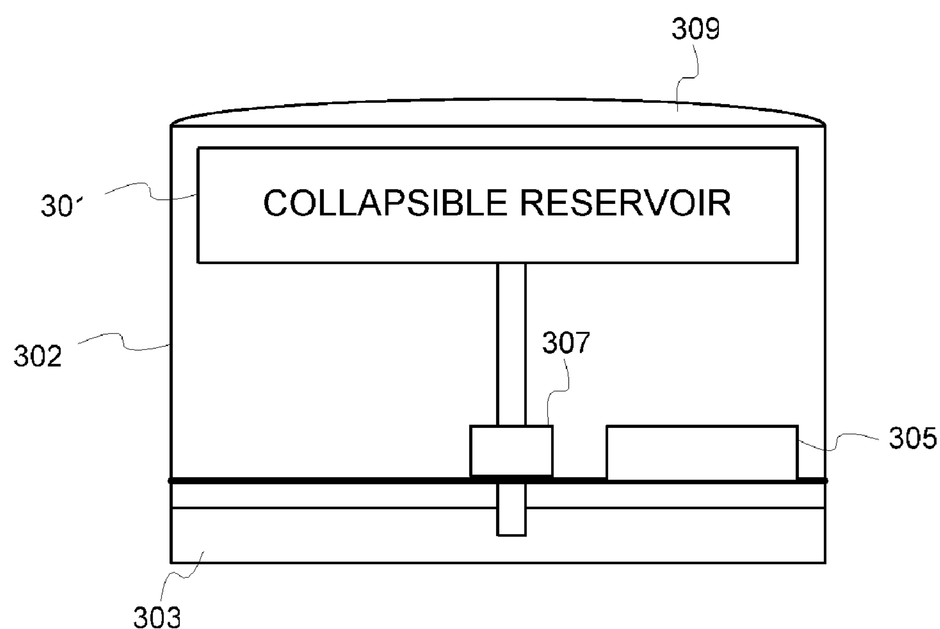
FIG. 3 is a schematic illustration of a drug delivery device in accordance with the present invention. Alternatively, permeation through the skin may be assisted by using micro-fabricated structures commonly referred to as Micro-needles, heating devices, iontophoretic devices, or sonophoretic devices that are attached to this device.

An exemplary implementation (shown in FIG. 3) comprises a collapsible drug reservoir 301, an expandable waste reservoir 305, a micro-pump 307, electronics for automation, a display 309, and a highly permeable membrane 303. Further, a heating element or a gas or air blowing apparatus may be used to assist evaporation of liquids into the waste reservoir or the environment. An exemplary system is described in a United Kingdom patent entitled Transdermal Drug Delivery and Method filed on Sep. 13, 2004, Application Number PCT/IB2004/002947, which is incorporated herein by reference. The drug reservoir 301 will contain between about 0.4 ml and 4 ml of drug formulation. A tiny, miniaturized pump 307 is activated at pre-programmed times and releases a predefined amount of drug formulation into the drug chamber, where the formulation comes into contact with diffusion matrix. This diffusional matrix is in intimate contact with a highly permeable membrane. This membrane rests on the skin, and provides for even diffusion of the drug over the device's drug absorption surface area. This membrane works effectively with, and can be coated with, an adhesive, hydrogel or polymer substance, which allows for rapid transport kinetics. In operation, when the administration of the drug needs to be discontinued, the remaining drug formulation is either removed or evaporated from the membrane area via the waste receptacle 305 containing a desiccant, containing a hydrophilic substance (hydrogel) or the device is taken off. Further, to achieve chronopharmacological drug delivery for drugs that may not passively pass through the skin adequately, the above described device may use permeation enhancers whereby permeation through the skin is assisted, such as mechanical permeation enhancers that include micro-fabricated structures commonly referred to as Micro-needles, or heat, or iontophoresis, sonophoresis, (together referred to as the Mechanical Permeation Enhancers) or a wide range of chemical permeation enhancers.

Figure 4:
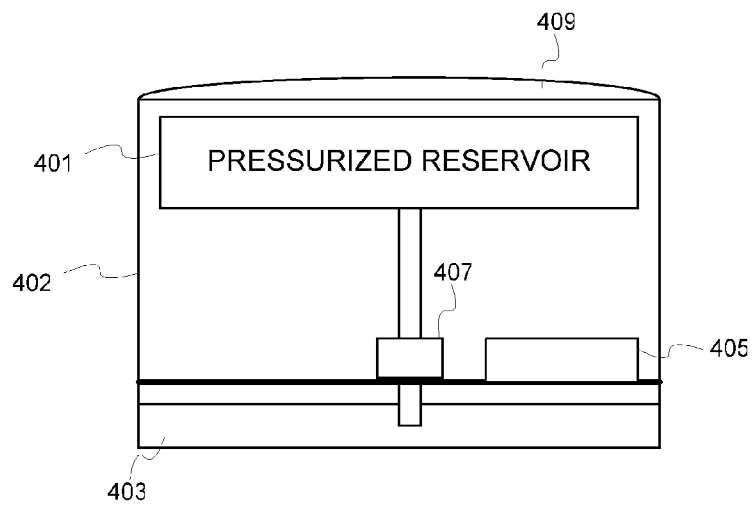
FIG. 4 is a schematic illustration of an alternative drug delivery device in accordance with the present invention. Alternatively, permeation through the skin may be assisted by using micro-fabricated structures commonly referred to as Micro-needles, heating devices, iontophoretic devices, or sonophoretic devices that are attached to this device.

In an implementation shown in FIG. 4, a pressurized drug reservoir 401 is used which minimizes or eliminates need for a micropump. Electronics control a valve that allows controlled quantities of the drug to be applied to the drug chamber where the formulation comes into contact with highly permeable membrane. The implementation shown in FIG. 4 further includes display 409, housing 402, chamber 407 expandable waste reservoir 405. Further, to achieve chronopharmacological drug delivery for drugs that may not passively pass through the skin adequately, the above described device may use permeation enhancers whereby permeation through the skin is assisted, such as mechanical permeation enhancers that include micro-fabricated structures commonly referred to as Micro-needles, or heat, or iontophoresis, sonophoresis, (together referred to as the Mechanical Permeation Enhancers) or a wide range of chemical permeation enhancers.

The construction and use of transdermal patches for the delivery of pharmaceutical agents is known. See, for example, U.S. Pat. No. 5,370,635, the disclosure of which is incorporated herein by reference. Such patches may be constructed using a saturated media, pressurized reservoirs, or unpressurized reservoirs with micropumps for continuous, pulsatile, or on-demand delivery of an active material.

For example, when administering a an active compound pursuant to a chronopharmacological dosage profile as set forth herein, using a programmed, transdermal, pulsatile drug delivery device, a pharmaceutically acceptable composition of an active material may be combined with either mechanical skin penetration enhancers including, but not limited to, micro-fabricated structures commonly referred to as Micro-needles, heat, iontophoresis, or sonophoresis, or a wide range of chemical permeation enhancers such as oleic acid, ethanol, amino acids, oleyl alcohol, long chain fatty acids, propylene glycol, polyethylene glycol, isopropanol, ethoxydiglycol, sodium xylene sulfonate, ethanol, N-methylpyrrolidone, laurocapram, alkanecarboxylic acids, dimethylsulfoxide, polar lipids, N-methyl-2-pyrrolidone, and the like, which increase the permeability of the skin to the active material and permit the active material to penetrate through the skin and into the bloodstream.

Pharmaceutically acceptable compositions may be combined with one or more agents including, but not limited to, alcohols, moisturizers, humectants, oils, emulsifiers, thickeners, thinners, surface-active agents, fragrances, preservatives, antioxidants, vitamins, or minerals.

Device-skin interface coupling media and/or control membranes include, but are not limited to, ethylcellulose, hydroxypropyl cellulose, poly (ethylene co-vinyl acetate), polyvinyl pyrrolidone, poly (ethylene oxide), poly (ethylene vinyl alcohol) and the like, to provide the composition in gel or hydrogel form, which may be dissolved in solvents such as water, methylene chloride or ethanol evaporated to the desired viscosity, and then applied to backing material to provide a patch. The control membranes can be any of the conventional materials such as microporous polyethylene, polyethylene co-vinyl acetate (EVA copolymer), polyurethane and the like.

Chronopharmacokinetics is defined as the predictable changes observed in the plasma levels of drugs and in the parameters used to characterize the pharmacokinetics of a drug. Studies on animals and humans indicate that the $C_{max}$, $T_{max}$, AUC and half-life often vary as a function of the hour of administration of the drug. Table 1 presents a list of medications for which temporal changes in pharmacokinetics have been documented.

TABLE 1

Drugs with documented time-dependent changes in pharmacokinetics*

| CLASSES OF DRUGS | SPECIFIC MEDICATIONS |
|---|---|
| Analgesic and NSAID | aspirin, sodium salicylate, acetaminophen, ketoprofene, phenyl butazone, indomethacin |
| CNS Drugs | hexabarbitol, carbamazepine, clorazepate, diazepam, lorazepam, midazolam, triazolam, amitryptiline,, sodium valproate |
| Cardiovascular Drugs | atenolol, metoprolol, lidocaine, dipyridamole, digoxine |
| Anti-asthmatic Drugs | aminophylline, theophyline, terbutaline |
| Antibiotic | ampicillin, erythromicin, griseofulvin, cefoxizime |
| Anti-cancer Agents | cisplatin |

*Labrecque, G. et al. Chronopharmacokinetics. Pharmaceutical News, 4 (2) 17-21 (1997)

We have carefully identified specific drugs and diseases because they have the following attributes: (i) Chronopharmacology is critical to optimized dosing but is not being implemented because no automated transdermal system exists, and (ii) these drugs can be transdermally absorbed passively (i.e., without the need for external modulation or pre-treatment such as sonophoresis, iontophoresis, electroporesis, microneedles, etc. or other permeation enhancement. Example substances include caffeine and ephedrine, and a variety of over-the-counter (OTC) and prescription stimulants (for treating fatigue, sleep disorders, attention deficit disorders and a variety of other conditions) in addition to herbal supplements, nicotine (for smoking cessation), nitroglycerin (for treating heart attack and strokes), fentanyl (for treating chronic pain), albutamol (for treating asthma), and selegiline (for treating depression, attention deficit disorder or Parkinson's disease). Exemplary chronopharmacological systems that can make use of the present invention are summarized in Table 2.

TABLE 2

Examples of disease states for ChronoDose ™ application

| THERAPEUTIC AREA | DISEASES/ CONDITION | CHRONO-PHARMACOLOGY RATIONALE |
|---|---|---|
| Cancer | Various forms | Chemotherapy may be more effective and less toxic if drugs are administered at carefully selected times that take advantage of tumor cell cycle times while less toxic to normal tissue. |
| Cardiovascular | Angina | Angina (variant) attacks occur 30 times more often between 2:00 a.m. and 4:00 a.m. → Larger doses of Nitroglycerin early in the morning |
| | Heart Attacks and Strokes | Heart attacks and strokes are most likely between 6:00 a.m. and Noon. → Cardiovascular active drugs before waking. |
| | Hypercholesterolemia | A circadian rhythm occurs during hepatic cholesterol synthesis. Cholesterol synthesis is generally higher during the night than during daylight. Studies with HMG CoA reductase inhibitors have suggested that evening dosing is more effective than morning |

TABLE 2-continued

Examples of disease states for ChronoDose ™ application

| THERAPEUTIC AREA | DISEASES/ CONDITION | CHRONO-PHARMACOLOGY RATIONALE |
|---|---|---|
| | | dosing. → Simvastatin in evening and during the night. |
| | Hypertension | Automatically and precisely release clonidine or other hypertension drugs in peak amounts to offset the peak symptoms associated with the dangerous morning symptoms. → Clinidine, Captopril or other medication in the morning. |
| CNS Degenerative Disorders | Parkinson's Disease | Automated dosing for patient compliance →Selegiline, Benztropine, Apomorphine |
| | Alzheimer's Disease | Automated dosing for patient compliance →Rivastigmine, Memantine |
| Diabetes | Diabetes (Type II) | Automated dosing for elderly patient compliance. Oral medication is poorly absorbed. → Miglitol before meals. Glibenclamide |
| Epilepsy | Epileptic seizure | Epileptic seizures are most likely between 6:00 a.m. and 7:00 a.m. → Gabapentan or other Epileptic drugs before waking up |
| Pulmonary | Asthma | Asthma attacks are 100 times more likely between 4:00 a.m. and 6:00 a.m. Adrenaline and Cortisol are virtually absent at night. → Albuterol or Tulobuterol in early morning. |
| Pain | Acute Pain | Neurological pain is worst between 3:00 a.m. and 8:00 a.m → Fentanyl in the middle of night. |
| | Migraine Headaches and/or Cluster headaches | Migraine headaches usually begin and occur between 8:00 a.m. and 10:00 a.m. Cluster headaches start earlier, around 4:00 a.m. → Zolmitriptan or dihydroergotamine in the middle of night. |
| Mental Health | Depression | Selegiline at night can create sleeping disorders (nightmares), but depression symptoms are high immediately upon waking up → Selegiline before waking up |
| Inflammation | Rheumatoid Arthritis, Osteoarthritis | Worst upon awakening. Cortisol and anti-inflammatory hormones are very low at night → Indomethacin or Valdecoxib before waking up. |
| Women's Health | Tocolytic Therapy | Programmed-in-time administration of tocolytic medication relative to the circadian rhythm in uterine contractility to avert preterm labor and birth. → Nifedipine, Terbutaline or Ritodrine synchronized with uterine contractions. |
| OTC | Smoking Cessation | Nicotine at night creates sleeping disorders (nightmares), but cravings are the highest immediately upon waking → Nicotine before waking up. |
| | Circadian rhythm sleep disorders (CRSD) and Morning Lethargy | Adrenaline is lowest in the morning, making early morning waking uncomfortable and difficult for many people.→ OTC Stimulant before waking |
| | Insomnia | Some sleep medications induce drowsiness but do not provide for continuous sleep in sensitive patients. → Pulsatile and low dose delivery of sleep medication will provide continuous sleep. |
| | Peptic Ulcer Disease | Gastric acid secretion increases in late afternoon and early night. Also, partial nocturnal resistance to $H_2$-blockade has been noted. → $H_2$-blockers (ranitidine, cimetidine, famotidine, roxatidine, nizatidine) during the night. Drugs other than $H_2$-blockers or antibiotics during the night. |
| | Jet lag Shift work | Melatonin can be used to reset circadian rhythms. |
| | Colds and Flu | Heaviest symptoms overnight and in the morning. → Cold/Flu medicine during the night. Triprolidine, Doxylamine |
| | Supplements/weight loss | Vitamins and Supplements are best administered in low doses over the course of the day to be most effective. |

Using this system the present invention can preprogram the times and amount of each dosage by precisely controlling the amount of drug exposed to the skin during each dosing. This feature is advantageous when a drug is best administered during sleep, e.g., 1 to 2 hours before waking up. The present invention precisely counteracts peak disease symptoms and increase patient compliance.

Figure 2A:
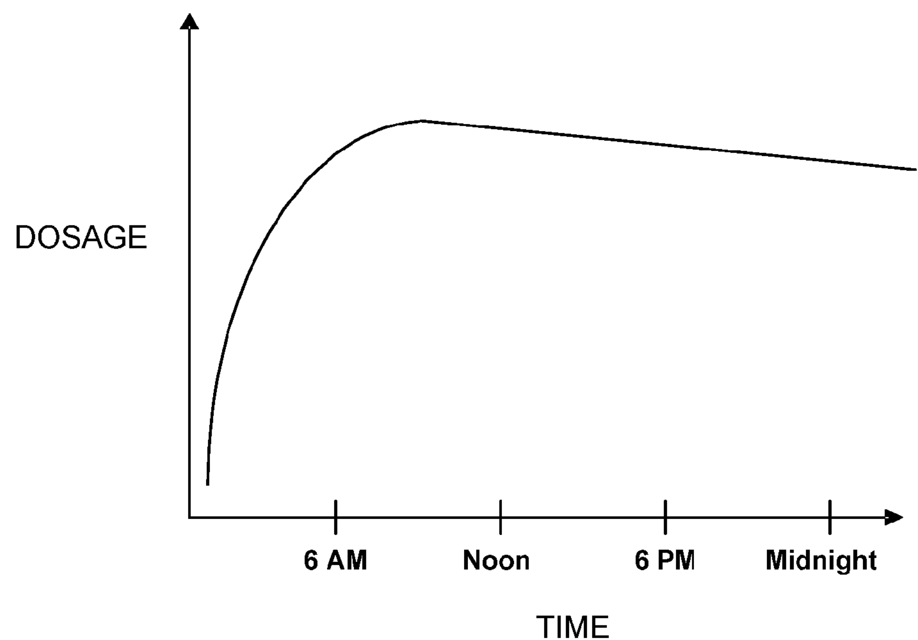
FIGS. 2A-2B illustrate comparative drug release profiles demonstrating operation of the present invention.
Figure 2B:
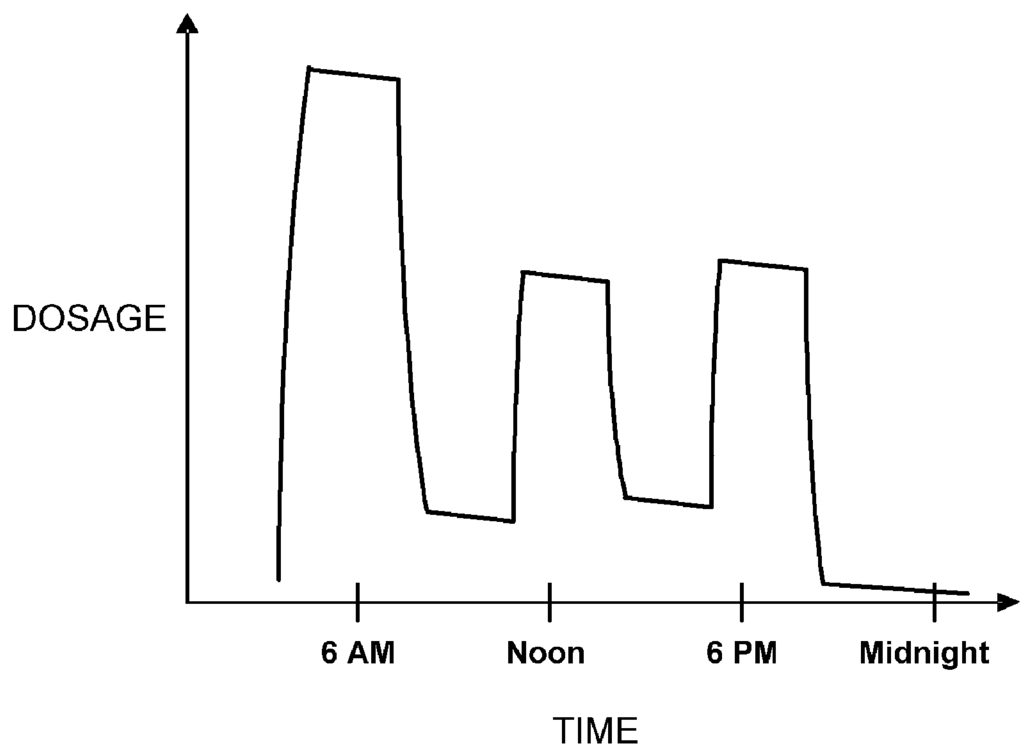

The present invention represents the first true non-invasive chronopharmacological drug delivery device. While current transdermal applications are restricted to the dosage profile shown in FIG. 2*a*, the automated implementation of the present invention can be programmed for a variety of drug delivery patterns to achieve customized patient dosing regiments for optimal therapy (FIG. 2*b*).

There are many advantages for a controlled transdermal release of an active material such as a drug. As used herein, the term 'controlled' or 'sustained' release of an active material includes continuous or discontinuous, linear or non-linear release of the active material according to a programmed schedule. Among the advantages of controlled release are the convenience of a single application for the patient, avoidance of peaks and valleys in systemic concentration which can be associated with repeated injections, the potential to reduce the overall dosage of the active material, lower body stress, and the potential to enhance the pharmacological effects of the active material. A lower, sustained dose can also prevent adverse affects that are occasionally observed with infusion therapy. In addition to significantly reducing the cost of care, controlled release drug therapy can free the patient from repeated treatment or hospitalization, thus offering the patient greater flexibility and improving patient compliance.

A controlled release formulation of certain drugs also provides an opportunity to use the drug in a manner not previously exploited or considered. The present invention is particularly advantageous when (i) known chronopharmacological information indicates that a drug's effects can be optimized when administered in a defined dosage at a predefined time or times, and/or (ii) patient compliance with the dosing regimen is greatly increased due to automation, i.e. doses are required at inopportune times, i.e. at night while sleeping.

The present invention may be used to treat, cure, prevent, control or alleviate a wide range of conditions and symptoms. For example, the drug delivery regimen of the present invention is administered to treat a condition selected from the group consisting of vitamin and/or mineral deficiency, Cancer, Addiction, Arthritis, Parkinson's Disease, Attention Deficit Disorder, Cardiovascular Disorder, Cold/Flu Symptoms, Pain, Childhood Bronchial Asthma, Peptic Ulcer, Post-operative Recuperation, and so forth as shown below.

Applications

ArisePatch™

A contemplated consumer product is the ArisePatch™. Most people experience difficulty and discomfort when waking early in the morning. According to a 2002 National Sleep Foundation poll 49% of US adults age 18-29 have trouble waking in the morning and 41% of US adults age 30-64 have trouble waking in the morning. There are 165,000,000 adults in the US alone age 18-64; meaning approximately 74,250,000 US adults age 18-64 have trouble waking in the morning.

Figure 5:
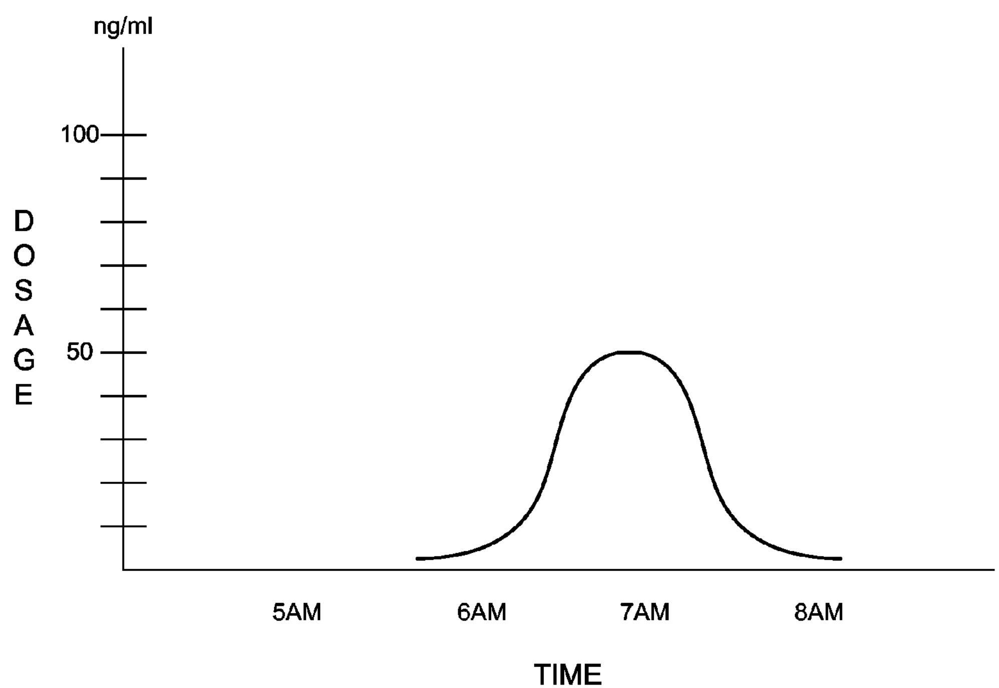
FIG. 5 shows an exemplary administration profile for a stimulant delivery system.

Chronotherapeutic Rationale:

The ArisePatch implementation of the present invention allows individuals, while asleep, to have an over-the-counter (OTC) or prescription stimulant automatically administered during a 1-2 hour pre-wake-up period. FIG. 5 illustrates an exemplary stimulant administration profile showing a blood plasma level of ephedrine in nanograms per milliliter on the vertical axis, with time on the horizontal axis. Stimulant concentrations will reach peak levels immediately prior to having to wake. Immediately upon waking up the individual will be alert and feel well rested. The ArisePatch™ will eliminate the typical discomfort or difficulty associated with getting up early. This functionality is attractive to employed people getting up for work to ensure punctuality, and just about anyone who wants to offset morning discomfort associated with a late night, jet lag, or sickness.

Applications

Smoking Cessation

Example

Nicotine

Nicotine replacement has been the most frequently used therapy to support smokers in their effort to quit. Smokers report that the craving for a cigarette is greatest immediately upon waking in the morning. The time elapsed between wakening and the first cigarette is the best indicator of addiction. For most smokers this time only a few minutes. Additionally, research has shown that nicotine transdermal delivery is influenced by chronopharmacokinetics. Nicotine patch design should compensate by decreasing the dose at night as well as increasing the dose in the morning and after meals (Gries et al., 1998).

Chronotherapeutic Rationale:

Current nicotine patches cause severe sleep disturbances by releasing nicotine steadily throughout the night to ensure sufficient morning nicotine levels to offset the strong morning craving. It is widely accepted that current nicotine patches have a detrimental and common side effect—sleeping disorders, and insomnia, including persistent nightmares. Therefore, users are often forced to remove the patch in the evening before they go to bed. This eliminates sleep disturbances, but results in nicotine levels that are insufficient to offset the strong morning craving. This is a major drawback to current nicotine patches and many users relapse, resulting in a less efficient smoking cessation therapy. Current patches present the user with a difficult decision, choosing between nightmares and relief from the strong morning cravings.

Example

An exemplary product contemplated by the present invention is called Nicotine ChronoDose™ system. In accordance with the present invention, the system can begin to administer nicotine (or nicotine analogs or any other smoking cessation compound including but not limited to bupropion) automatically during a one-hour period immediately prior to waking. This will relieve the smoker's peak craving upon waking without causing nightmares and insomnia. We believe that this system clearly provides a superior method for smoking cessation.

Figure 6:
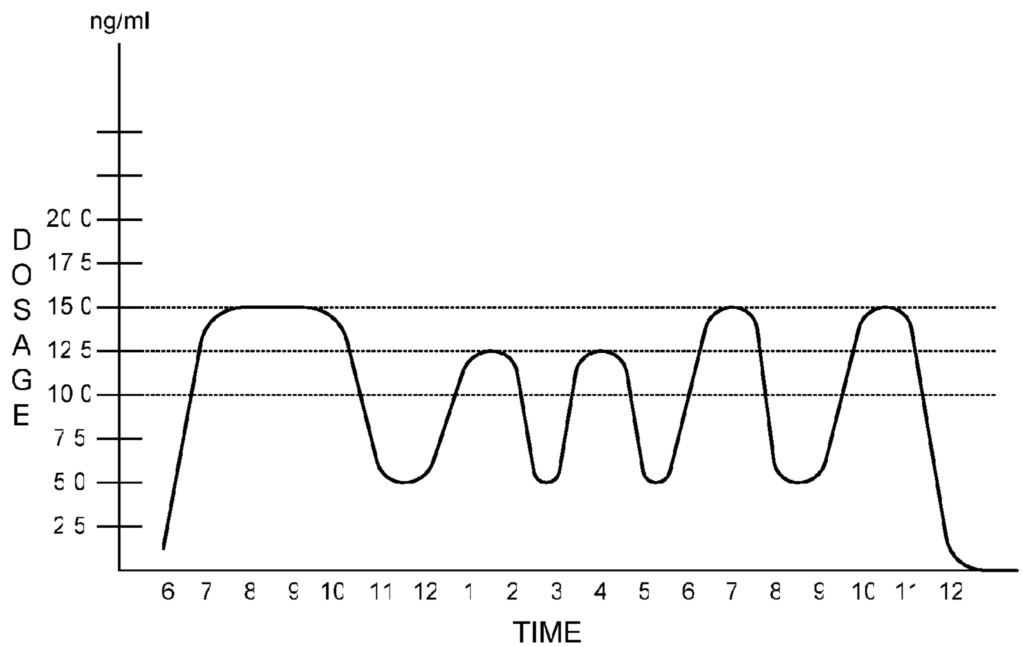
FIG. 6 shows an exemplary administration profile for a nicotine delivery system.

A more advanced nicotine replacement system than that described above is worn for three days at a time and is programmed to release nicotine in a daily rhythmic pattern such as shown in FIG. 6 to offset peaks in a smoker's cravings. FIG. 6 illustrates an exemplary nicotine administration profile showing a blood plasma level of nicotine in nanograms per milliliter on the vertical axis, with time on the horizontal axis. This implementation will reduce nicotine dependency by administering pre-programmed levels of nicotine pursuant to typical smoking patterns. For instance many smokers report that cravings for a cigarette are greatest upon waking up, after lunch, mid afternoon, after dinner and before bedtime. This implementation of the present invention will automatically release larger doses of nicotine to offset peak cravings and no nicotine when cravings are typically at a minimum. The present invention may be delivered in a pre-programmed manner for each treatment regimen. The only involvement by the user will be the replacement of the 'reservoir' every three days, and the replacement of the platform housing as needed.

This implementation represents a tremendous move forward in nicotine replacement therapy, and is far superior to the old-technology systems that simply release the same amount of nicotine all day and night. With the present invention, one can systematically decrease a smoker's tolerance without increasing dependence (the result of a constant flow) and better wean a smoker off nicotine. This will allow the smoker to better 'tailor-down' and decrease the amount of nicotine he needs to quit. Modern smoking cessation is much more than nicotine replacement therapy. Programs also include weight control, diet and psychological support. The present invention fits well into these programs, since it addresses the key component of being able to quit smoking by efficiently countering the withdrawal symptoms while doing away with the negative side effects of current nicotine replacement therapy systems, namely sleep disturbance.

Applications

Angina

Example

Nitroglycerin

Research shows that variant angina occurs 30 times more often between 2:00 a.m. and 4:00 a.m. ('critical angina phase') than at any other time of the day. Nitroglycerin effectively combats angina attacks, if administered in optimal doses. Current nitroglycerin patches exist, but they can only release a constant amount of nitroglycerin steadily over time. Current patches cannot tailor the release of nitroglycerin to optimize treatment by releasing more nitroglycerine precisely during the critical angina phase to offset these peak symptoms.

In addition, nitroglycerine loses its effectiveness and requires higher and higher dosages when administered constantly. Our bodies become tolerant to it. Current systems cannot stop or decrease the release of nitroglycerine when disease symptoms are lowest. Thus, these current 'dumb' patches cannot offset the critical angina phase by releasing more of the drug, nor can they shut down or stop nitroglycerin administration when the body doesn't need it. It is a 'one dose fits all' type of scenario once each "dumb" patch is applied to the patient.

Chronotherapeutic Rationale:

The method in accordance with the present invention utilizes an automated transdermal system in order to transdermally administer more nitroglycerin during the critical angina phase to ensure adequate offset of these symptoms and less nitroglycerin when it is not needed so that no tolerance builds up. Our method utilizes a 'smart' patch medicine system at this time to offset these peak critical phases in the disease cycle arising due to the human body's circadian rhythm.

The pre-programmable automated transdermal system is worn around the wrist—like a watch (or the forearm arm or ankle) and releases nitroglycerin in optimal dosages at times that are optimally synchronized. This is pursuant to a pre-programmed and tailored dosage profile. Current nitroglycerin patches only have the capability to release a constant dose of nitroglycerin over a period of time. Current nitroglycerin patches simply cannot alter or vary dosages to increase dosages at different times of the day, and decrease dosages at other times of the day.

Example

The nitroglycerin system in accordance with the present invention has three primary advantages over current nitroglycerin patches. First, the system automatically and precisely releases nitroglycerin in peak amounts to offset the peak symptoms of morning attacks occurring during the critical angina phase. Current nitroglycerin patches have release rates that stay constant and do not increase to offset critical phases, and do not decrease as symptoms decrease. Second, our system solves the tolerance issue by releasing less (or no) nitroglycerin in off-peak hours, and then releasing nitroglycerin at just the right time so that it is present during critical periods, without increasing tolerance. Third, our system accomplishes 1 and 2 above automatically, without the need for a patient to wake up to take a drug at this critical phase, which does away with the need for any increased patient compliance.

The nitroglycerin system represents an ideal delivery system for patients who use nitroglycerin regularly for the treatment and/or the prevention of heart attacks and strokes. Patient compliance regarding the timing and dose of heart attack medication is crucial. Patient non-compliance with physician's instructions for this is often a cause of re-hospitalization, according to the US Department of Health and Human Services. The system solves this problem, and will decrease the need for re-hospitalization by dramatically increasing patient compliance.

This system can be either an 'wear each night and remove in the morning' system, whereby it only releases nitroglycerin automatically to offset the critical angina phase in the morning, or a 'total solution' system, that is worn for a period of 24 hours to several days, and that administers nitroglycerin in tailored amounts and at tailored times as synchronized with the body's circadian rhythm (and conveniently taken off while showering or swimming).

The system is an innovative new drug therapy for angina. With the advantage of optimized and automated time and dose administration synchronized with a person's circadian rhythms, the system in accordance with the present invention ensures that nitroglycerin will circulate in the bloodstream exactly when the patient needs it, and without any build up tolerance. For these reasons, the present invention is superior to current steady release nitroglycerin patches. Our system's increased advantages are extremely relevant for those patients with moderate to severe angina.

Figure 7:
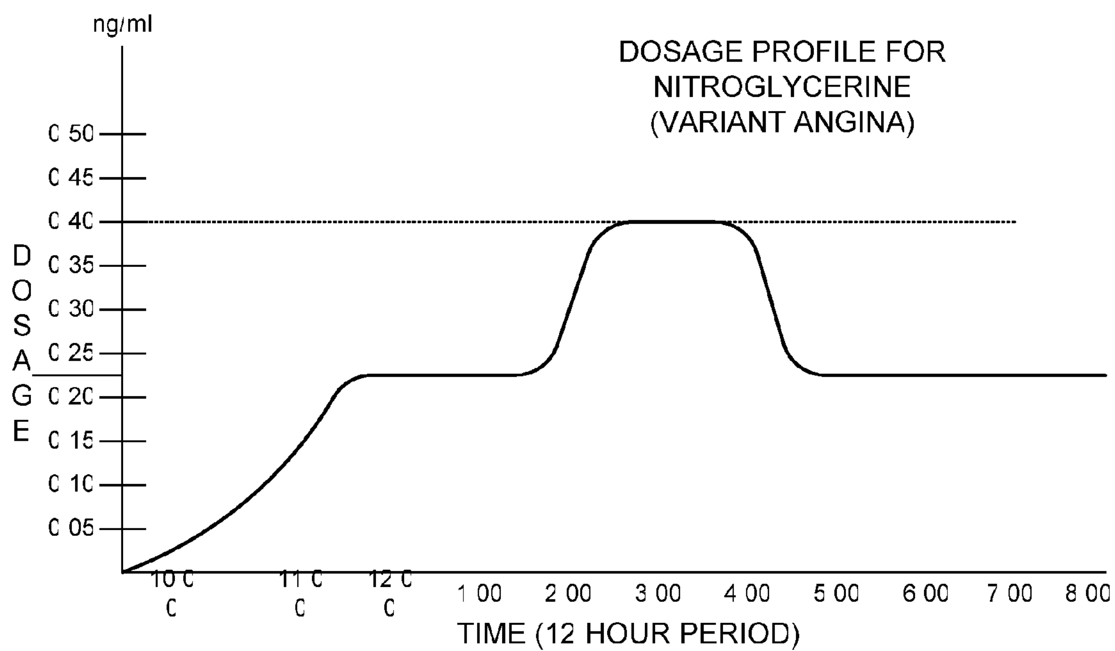
FIG. 7 shows an exemplary administration profile for a nitroglycerin delivery system tailored to treat variant angina attacks.

FIG. 7 shows an exemplary administration profile for a nitroglycerin delivery system tailored to treat variant angina attacks or angina pectoris. This type of angina attack has a peak frequency in many patients between the hours of 2:00 and 4:00 AM. This is a particularly difficult time to wake up to take a drug such as nitroglycerin. In accordance with the present invention an administration profile substantially like that shown in FIG. 7 is automatically administered. In FIG. 7 the vertical axis indicates blood plasma level in nanograms per milliliter, and the horizontal axis indicates time from 10:00 PM through the night to 8:00 AM.

Figure 8:
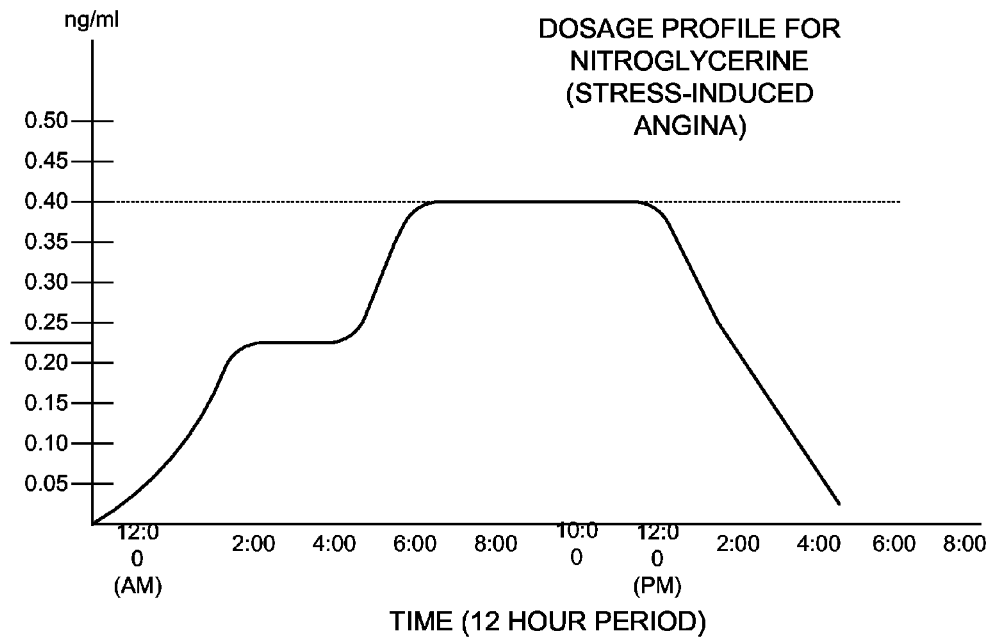
FIG. 8 illustrates an exemplary administration profile for a nitroglycerin delivery system tailored to treat stress-induced angina attack.

FIG. 8 illustrates an exemplary administration profile for a nitroglycerin delivery system tailored to treat stress-induced angina attack. In FIG. 8 the vertical axis indicates blood plasma level in nanograms per milliliter, and the horizontal axis indicates time from 12:00 AM through the day until about 4:00 PM. The administration profile shown in FIG. 8 provides a high blood plasma concentration throughout the waking hours of a day when stress is likely occur.

Applications

Arthritis

Examples

Indomethacin, Valdecoxib

An automated, and programmed, pulsatile drug delivery regimen is desired to in order to increase drug concentrations automatically in the morning, just before a person awakes and the symptoms of arthritis are the worst. Later, towards mid-day, the drug concentration is also increased. Then in the evening, the drug dose is increased prior to bedtime.

Chronotherapeutic Rationale:

The most common forms, osteoarthritis and rheumatoid arthritis, both show distinctive circadian patterns of pain. While many people feel stiff for an hour or so after first getting up in the morning, people with osteoarthritis typically hurt most and have the most difficulty moving in the afternoon and evening. Those with rheumatoid arthritis almost always feel much worst in the morning. By dosing at night, early morning and mid-day, the benefits of non-steroidal anti-inflammatory drugs (NSAIDs) and cyclocoygenase-2 inhibitors (COX-2) can be maximized and side effects reduced.

Examples of medications for arthritis include:

Indomethacin (Indocin®)

Diclofinac (Voltarin® and Cataflam®)

Flurbiprofen (ANSAID®)

Celecoxib (Celebrex®)

Valdecoxib (Bextra®)

Acetomenophen (Tylenol®)

Oxaceprol

Example 1

Indomethacin (NSAID)

The primary adverse side effect of Indomethacin is gastrointestinal upset and bleeding. Therefore a transdermal arthritis patch would be a beneficial dosage form as opposed to oral tablets and capsules. Additionally, studies using indomethacin showed better efficacy and patient complience when dosed at night than when dosed at 8:00 am.

Theoretical unenhanced transdermal flux for indomethacin (Berner-Cooper predictive model) is 0.93 ug/cm$^2$/hr.

Thus, dosing could be optimized using the ChronoDose system. For example, pulsatile delivery should have blood plasma concentrations (BPC) as set forth below within the following ranges at the following times:

Peak 1 (Highest)

5:00 am-9:00 am: BPC should be in the highest therapeutic range of between 0.5-2.0 mcg/ml.

Peak 2 (Medium)

12:00 pm to 8:00 pm: BPC should be in the medium therapeutic range of between 0.25-1.5 mcg/ml.

Peak 3 (Highest)

8:00 pm-11:00 pm: BPC should be in the highest therapeutic range of between 0.5 to 2.0 mcg/ml.

Figure 9:
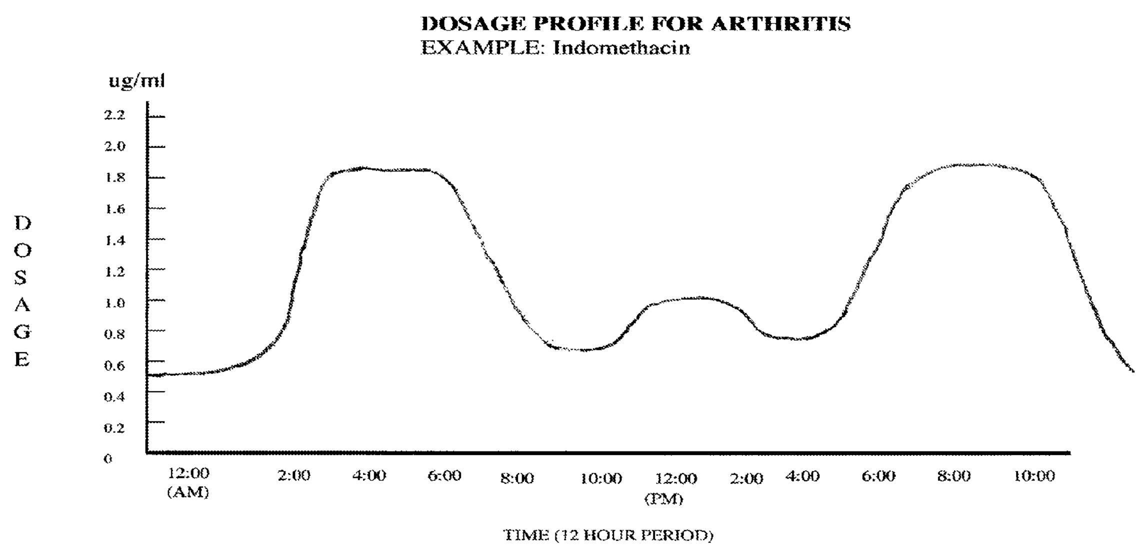
FIG. 9 illustrates an exemplary administration profile for an indomethacin delivery system tailored to arthritis.

The time/dose chart should appear as shown in FIG. 9

Example 2

Valdecoxib (COX-2 Inhibitor)

Like indomethacin, the primary adverse side effect of COX-2 inhibitors is gastrointestinal upset and bleeding. Therefore a transdermal arthritis patch would be a beneficial dosage form as opposed to oral tablets and capsules. Lower blood plasma concentrations of COX-2 inhibors delivered transdermally has been suggested as therapeutically equivalent to higher BPC obtained by oral dosing.

Thus, dosing could be optimized using the ChronoDose system. For example, pulsatile delivery should have blood plasma concentrations (BPC) as set forth below within the following ranges at the following times:

Peak 1 (Highest)

5:00 am-9:00 am: BPC should be in the highest therapeutic range of between 50-175 ng/ml.

Peak 2 (Medium)

12:00 pm to 8:00 pm: BPC should be in the medium therapeutic range of between 21-125 ng/ml.

Peak 3 (Highest)

8:00 pm-11:00 pm: BPC should be in the highest therapeutic range of between 50 to 175 ng/ml.

Figure 10:
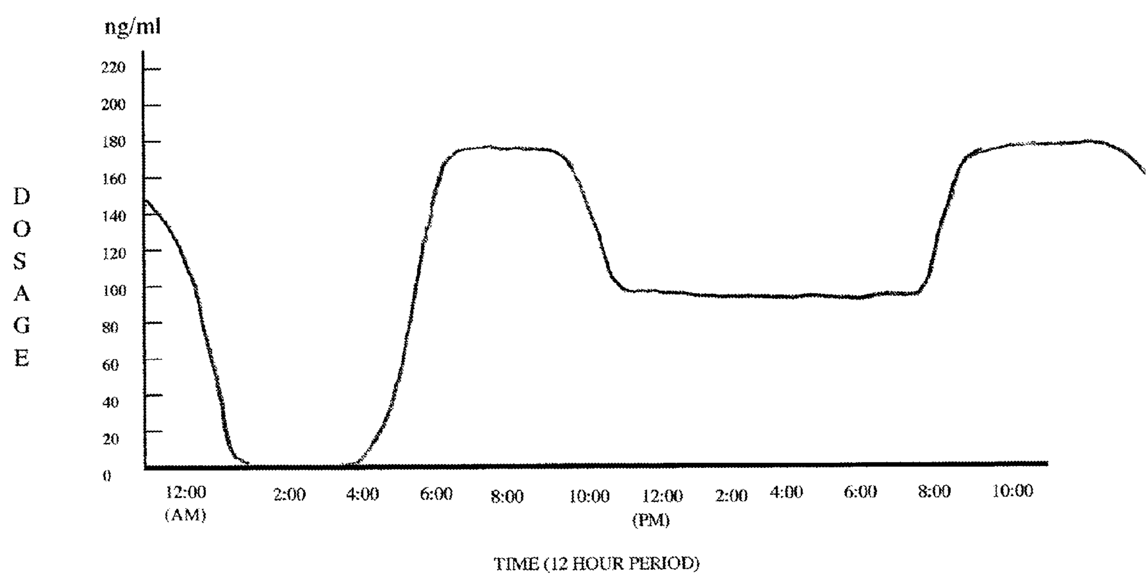
FIG. 10 illustrates an exemplary administration profile for a valdecoxib delivery system tailored to treat arthritis.

The time/dose chart should appear as shown in FIG. 10

Applications

Asthma

Example

Tulobuterol

The automated transdermal asthma system automatically administers a morning dose of albuterol, tulobuterol, salmeterol, beta 2 agonist or any other antiarrhythmic drug (an 'Asthma drug') to combat the peak symptom of morning asthma attacks known as the 'morning dip'.

Chronotherapeutic Rationale:

Asthma attacks occur 100 (one hundred) times more often between the hours 4 A.M. and 6 A.M., when most people are asleep. This is due to the early morning deterioration of respiratory function known as 'morning dip', which is the time of day that respiratory function is at its lowest. These early morning asthma attacks cause great distress to sufferers and care providers. The morning dip represents the dip in respiratory function at this time when asthma attacks are 100 times more likely to occur. Our system effectively combats the morning dip by releasing more Asthma drug at this time to offset this peak morning symptom. In other words, our 'smart' patch varies the level of drug in the bloodstream so that drug concentrations are highest when respiratory function is at its lowest.

Current 'dumb' asthma patches exist, but they can only release a constant amount of drug steadily over time. Current patches cannot tailor the release of drug to optimize treatment by releasing more drug precisely during the morning dip to offset these peak critical symptoms.

The Asthma system has two primary advantages over current patches. First, the system of the present invention utilizes its core competitive advantage to automatically and precisely release tulobuterol or other asthma drugs in peak amounts to offset the peak symptoms associated with the morning dip. Current patches have release rates that stay constant and do not increase to offset this peak critical phases, and do not decrease as symptoms decrease. Second, our system accomplishes 1 and 2 above automatically, without the need for a patient to wake up to take a drug at this critical phase, which does away with the need for any increased patient compliance.

The automated transdermal system for asthma is worn around the wrist like a watch (or the forearm arm or ankle) and releases albuterol or other asthma drugs in optimal dosages at times that are optimally synchronized, especially to offset the morning dip, pursuant to a pre-programmed and tailored dosage profile. Current Asthma patches only have the capability to release a constant dose over a period of time. Current Asthma patches simply cannot alter or vary dosages to increase dosages at different times of the day, and decrease dosages at other times of the day.

The system is an innovative new drug therapy for asthma. With its superior advantage of optimized and automated time and dose administration synchronized with our circadian rhythms, our system ensures that tulobuterol or another asthma drug will circulate in increased amounts in the bloodstream exactly when the patient needs it. For these reasons, our system is superior to current steady release patches. Our system's increased advantages are extremely relevant for those patients with moderate to severe asthma.

Figure 11:
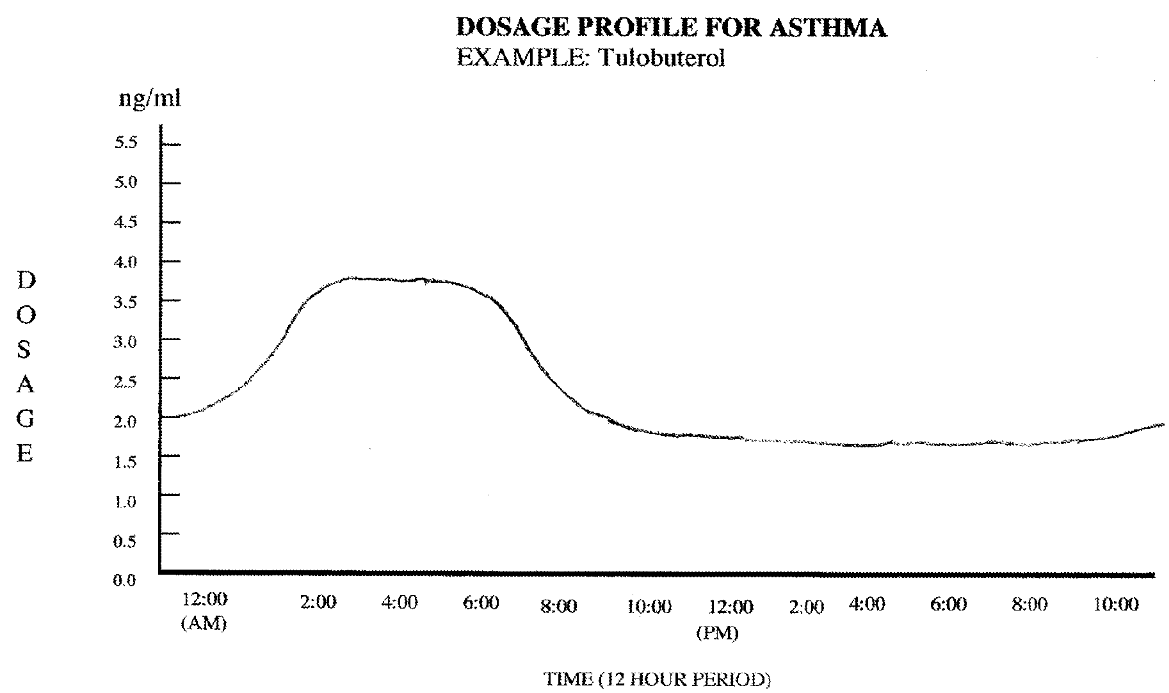
FIG. 11 illustrates an exemplary administration profile for a tulobuterol delivery system tailored to treat asthma.

The time/dose chart should appear as shown in FIG. 11.

Applications

Hypertension

Example

Clonidine

Current clonidine patches release the drug consistently over time. It cannot release more of the drug when symptoms are worst. People die most when the symptoms peak. Having the advantage of administering more of the drug when a patient needs it the most can mean the difference between life and death, especially in patients with moderate to severe high blood pressure.

Chronotherapeutic Rationale:

The automated transdermal system for hypertension has two primary advantages over current patches. First, our system utilizes its core competitive advantage to automatically and precisely release clonidine or other hypertension drugs in peak amounts to offset the peak symptoms associated with the dangerous morning symptoms. Current hypertension patches have release rates that stay constant and do not increase to offset this peak critical phases, and do not decrease as symptoms decrease. Second, our system accomplishes 1 and 2 above automatically, without the need for a patient to wake up to take a drug at this critical phase, which does away with the need for any increased patient compliance. The clonidine automated transdermal system utilizes clonidine, (or another hypertension drug) an effective drug that combats high blood pressure.

Example

The clonidine automated transdermal drug delivery system has an automated morning release of Clonidine to combat the peak symptom of morning heart attacks. Blood pressure differs at different times of the day. Blood pressure surges upon waking, and is lower by 20 to 30 percent while sleeping. Our preprogrammed automatic transdermal system utilizes its core competitive advantage by releasing clonidine in a tailored fashion to counter high blood pressure when symptoms are highest, while releasing less clonidine when symptoms are less severe.

Figure 12:
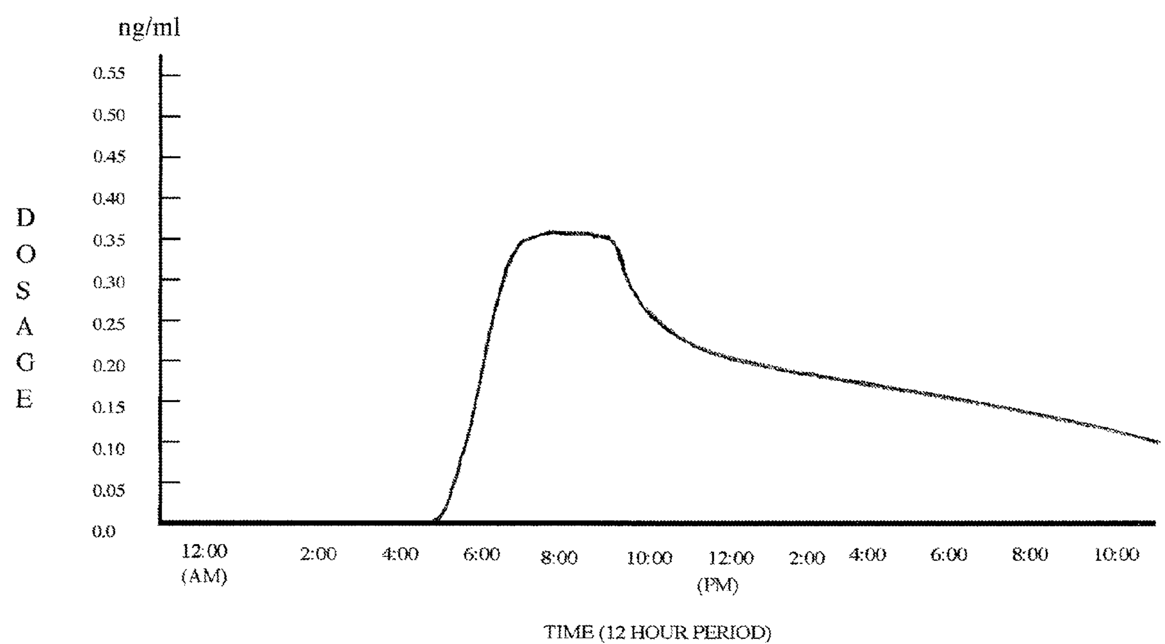
FIG. 12 illustrates an exemplary administration profile for a clonidine delivery system tailored to treat hypertension.

The time/dose chart should appear as shown in FIG. 12

Applications

CNS Degenerative Disorders

Example

Selegiline

Parkinson's Disease

Sleep disturbances in Parkinson's disease patients reveal alterations of circadian rhythms. Autonomic dysfunction, described in Parkinson's disease, reveals numerous alterations in circadian regulations including loss of circadian rhythm of blood pressure, increased diurnal blood pressure variability, and postprandial hypotension. Many biologic indices such as cortisol, catecholamines, and melatonin are also altered. Circadian rhythms in dopaminergic systems as well as possible daily fluctuations in kinetics of drug treatments are likely involved in such variations.

Chronotherapeutic Rationale:

Primary negative side effects of the selegiline patches are abnormal dreams, insomnia, and difficulty sleeping. We believe that by specifically refraining from administering selegiline at night, and utilizing our system's core competitive advantage to turn it on an hour or so before waking, we can do away with this negative side effect and still offset the critical phase of morning symptoms of depression. It has been reported that patients have increased symptoms of depression upon waking if the critical amount of Selegiline is not circulating through their system.

The selegiline automated transdermal drug delivery system gives an automated morning release of selegiline to combat the peak symptom of morning depression without the side effect of sleep disturbances. The system in accordance with the present invention is applied before bed. It does not release the drug until one or two hours before morning, so symptom of morning depression would be corrected by our system without subjecting the patient to sleep disturbances.

Figure 13:
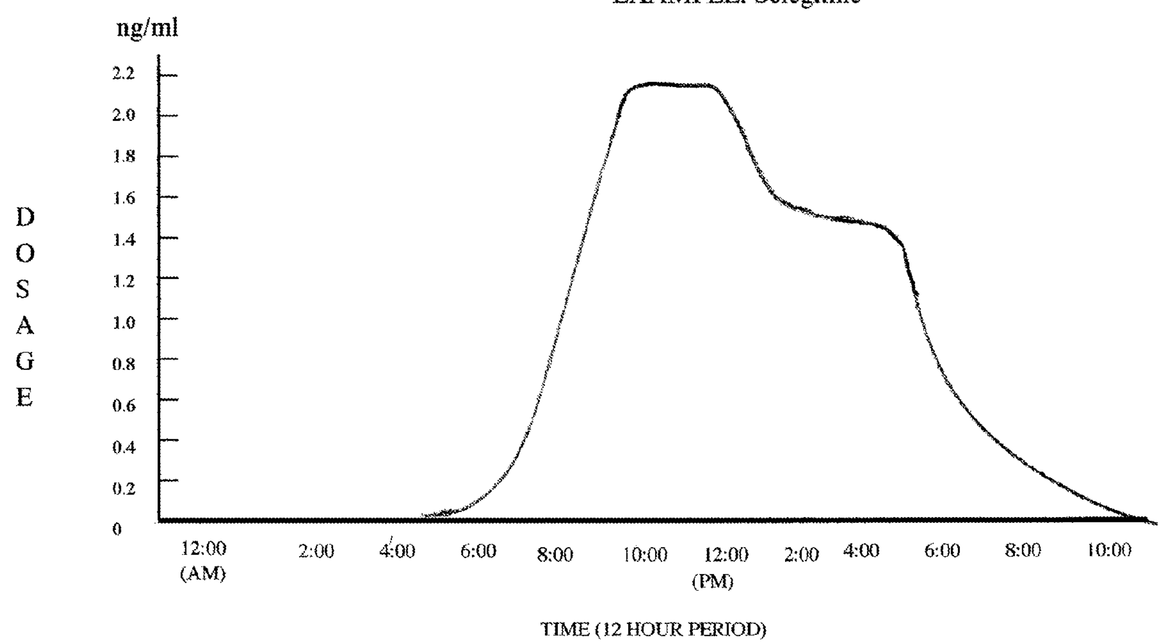
FIG. 13 illustrates an exemplary administration profile for a selegiline delivery system tailored to treat CNS degenerative disorders (Parkinson's Disease).

The time/dose chart should appear as shown in FIG. 13

Alzheimer's Disease

Selegiline is an effective MAO inhibitor for the treatment of depression, Alzheimer's and Attention Deficit Disorder. Currently oral selegiline produces many undesirable side effects. A transdermal form of selegiline, EMSAM™, is currently being developed. However, it also produces sleep disturbances as well. It is believed that the system in accordance with the present invention would be superior to conventional selegiline product delivery systems.

Chronotherapeutic Rationale:

Primary negative side effects of the selegiline patches are abnormal dreams, insomnia, and difficulty sleeping. We believe that by specifically refraining from administering selegiline at night, and utilizing our system's core competitive advantage to turn it on an hour or so before waking, we can do away with this negative side effect and still offset the critical phase of morning symptoms of depression. It has been reported that patients have increased symptoms of depression upon waking if the critical amount of Selegiline is not circulating through their system.

The selegiline automated transdermal drug delivery system gives an automated morning release of selegiline to combat the peak symptom of morning depression without the side effect of sleep disturbances. The system in accordance with the present invention is applied before bed. It does not release the drug until one or two hours before morning, so symptom of morning depression would be corrected by our system without subjecting the patient to sleep disturbances.

Figure 14:
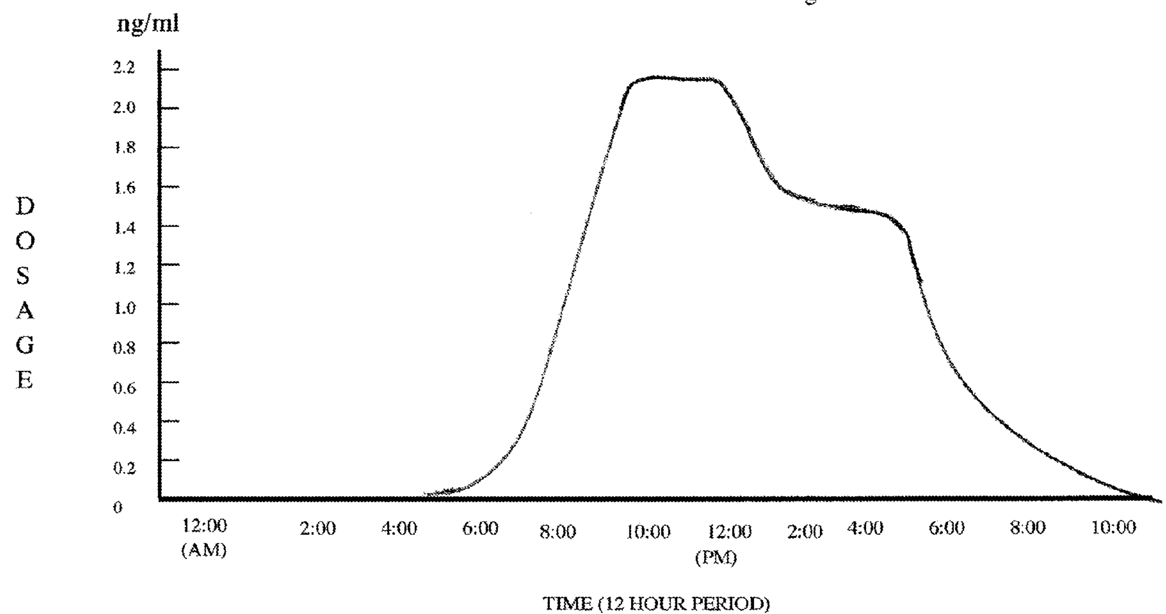
FIG. 14 illustrates an exemplary administration profile for a selegiline delivery system tailored to treat Alzheimer's Disease and attention deficit disorder.

The time/dose chart should appear as shown in FIG. 14

Applications

Attention Deficit Disorder

Example

Methylphenidate

Ritalin is indicated as an integral part of a total treatment program which typically includes other remedial measures (psychological, educational, social) for a stabilizing effect in children with a behavioral syndrome characterized by the following group of developmentally inappropriate symptoms: moderate-to-severe distractibility, short attention span, hyperactivity, emotional lability, and impulsivity.

Methylphenidate is usually administered in divided doses 2 or 3 times daily, preferably 30 to 45 minutes before meals. Patients who are unable to sleep if medication is taken late in the day should take the last dose before 6 p.m. Since the suggested first dose is early in the morning, it would be beneficial to automatically control the dosage.

Thus, dosing could be optimized using the ChronoDose system. For example, pulsatile delivery should have blood plasma concentrations (BPC) as set forth below within the following ranges at the following times:

Peak 1 (Highest)

6:00 am-8:00 am: BPC should be in the highest therapeutic range of between 8-25 ng/ml.

Peak 2 (Highest)

10:00 am to 12:00 pm: BPC should be in the highest therapeutic range of between 8-25 ng/ml.

Peak 3 (Highest)

3:00 pm-5:00 pm: BPC should be in the highest therapeutic range of between 8 to 25 ng/ml.

Figure 15:
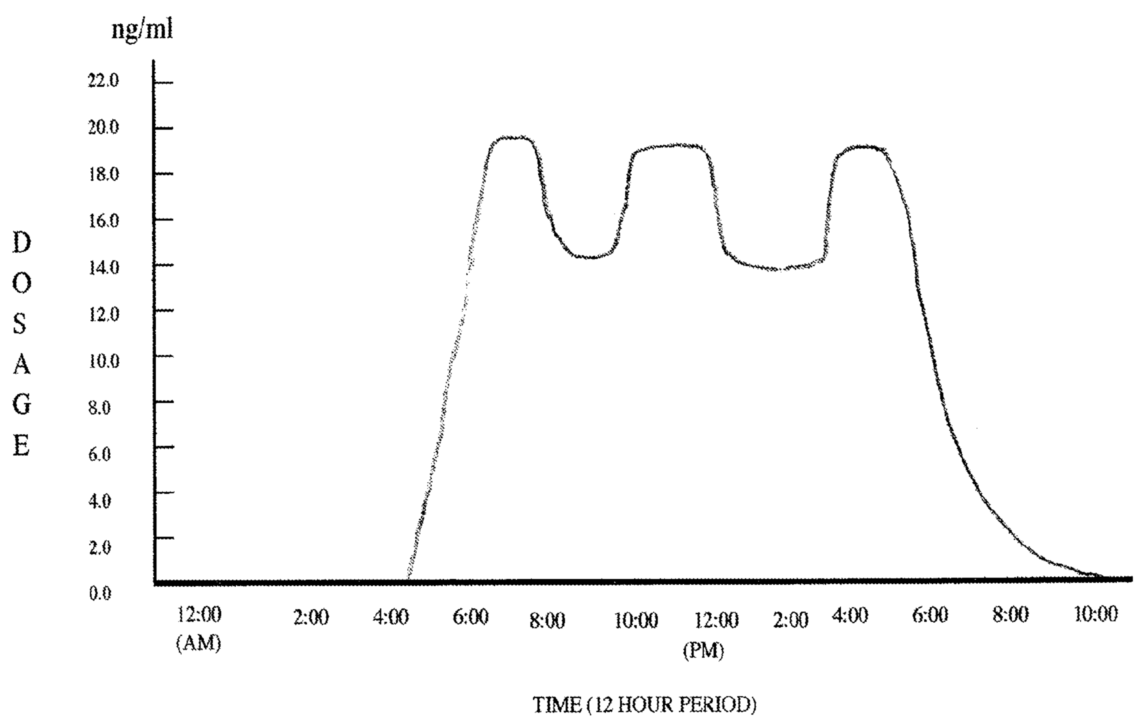
FIG. 15 illustrates an exemplary administration profile for a methylphenidate delivery system tailored to treat ADD.

The time/dose chart should appear as shown in FIG. 15

Applications

Depression

Example

Selegiline

Selegiline is an effective MAO inhibitor for the treatment of depression, Alzheimer's and Attention Deficit Disorder. Currently oral selegiline produces many undesirable side effects. A transdermal form of selegiline, EMSAM™, is currently being developed. However, it also produces sleep disturbances as well. It is believed that the system in accordance with the present invention would be superior to conventional selegiline product delivery systems.

Chronotherapeutic Rationale:

Primary negative side effects of the selegiline patches are abnormal dreams, insomnia, and difficulty sleeping. We believe that by specifically refraining from administering selegiline at night, and utilizing our system's core competitive advantage to turn it on an hour or so before waking, we can do away with this negative side effect and still offset the critical phase of morning symptoms of depression. It has been reported that patients have increased symptoms of depression upon waking if the critical amount of Selegiline is not circulating through their system.

The selegiline automated transdermal drug delivery system gives an automated morning release of selegiline to combat the peak symptom of morning depression without the side effect of sleep disturbances. The system in accordance with the present invention is applied before bed. It does not release the drug until one or two hours before morning, so symptom of morning depression would be corrected by our system without subjecting the patient to sleep disturbances.

Figure 16:
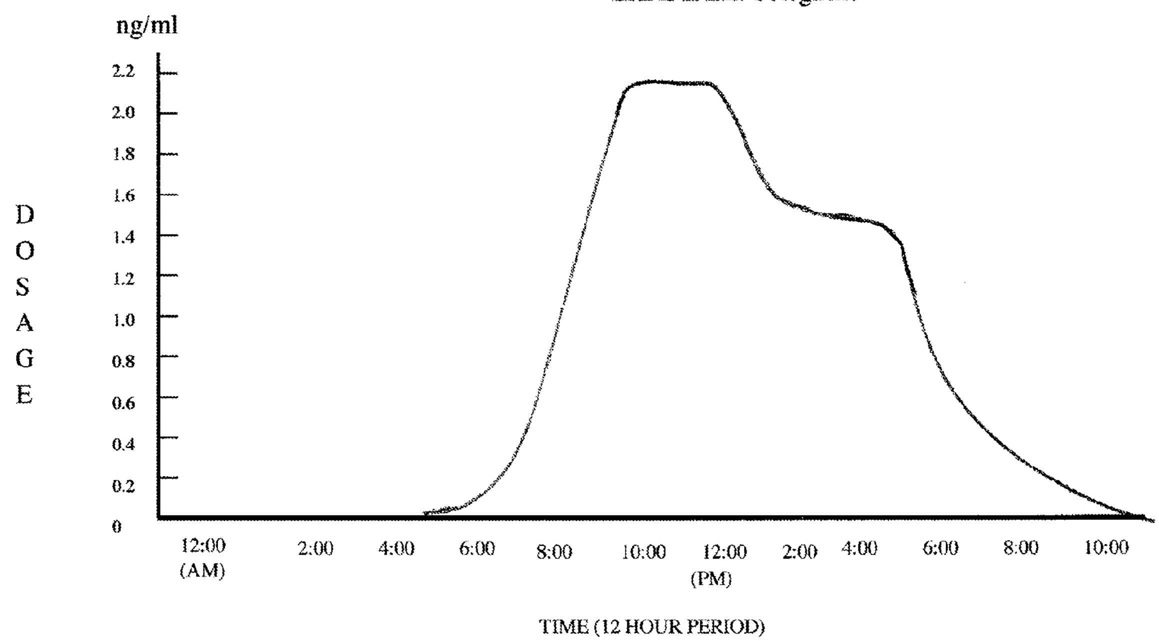
FIG. 16 illustrates an exemplary administration profile for a selegiline delivery system tailored to treat depression.

The time/dose chart should appear as shown in FIG. 16

Applications

Urinary Incontinence

Example

Oxtybutynin

An automated, and programmed, pulsatile drug delivery regimen is desired to in order to increase drug concentrations automatically at night while asleep, and to decrease concentrations during the daytime work hours, and again to slightly increase drug concentrations after work and prior to bed.

Chronotherapeutic Rationale:

The primary adverse side effect of Oxybutynin is daytime sleepiness, daytime attention and cognitive deficits, drowsiness, dizzyness, blurred vision, (must use caution when driving, operating machinery, or performing other hazardous activities). Therefore, it seems that a dose in the lower end of the therapeutic range should be administered during the daytime, with a slightly larger dose administered after working hours, and with an even higher dose administered during the sleeping hours.

This would reduce the potentially serious adverse side effect of daytime drowsiness and daytime cognitive impairment. This dosing regimen would also give the user a higher dose at night, when one sleeps. At this time, increased drowsiness would be advantageous as well as providing a period of undisturbed sleep due to the inhibition of urge incontinence.

Medications for incontinence include:

Oxybutynin (Ditropan® and Oxytrol®)

Tolterodine (Detrol®)

Duloxetine (Yentreve®)

Example 1

Oxybutynin

The mean maximum blood plasma concentration following oral dosing with 5 mg oxybutynin or transdermally with 39 mg is 3 ng/mL. Blood plasma concentration between 1 and 3 ng/ml Theoretical unenhanced transdermal flux for oxybutynin (Berner-Cooper predictive model) is 10.98 ug/cm$^2$/hr.

NOTE: Dose of current Oxytrol patches are 3.9 mg per day.

Thus, dosing could be optimized using the ChronoDose system. For example, pulsatile delivery should have blood plasma concentrations (BPC) as set forth below within the following ranges at the following times:

Peak 1 (Highest)

11:00 pm-7:00 am: BPC should be in the highest therapeutic range of between 2.5-4.5 ng/ml.

Peak 2 (Low)

7:00 am to 5:00 pm: BPC should be in the lowest therapeutic range of between 0.75-1.5 ng/ml.

Peak 3 (Medium)

5:00 pm-11:00 pm: BPC should be in the medium therapeutic range of between 1.5 to 2.5 ng/ml.

Figure 17:
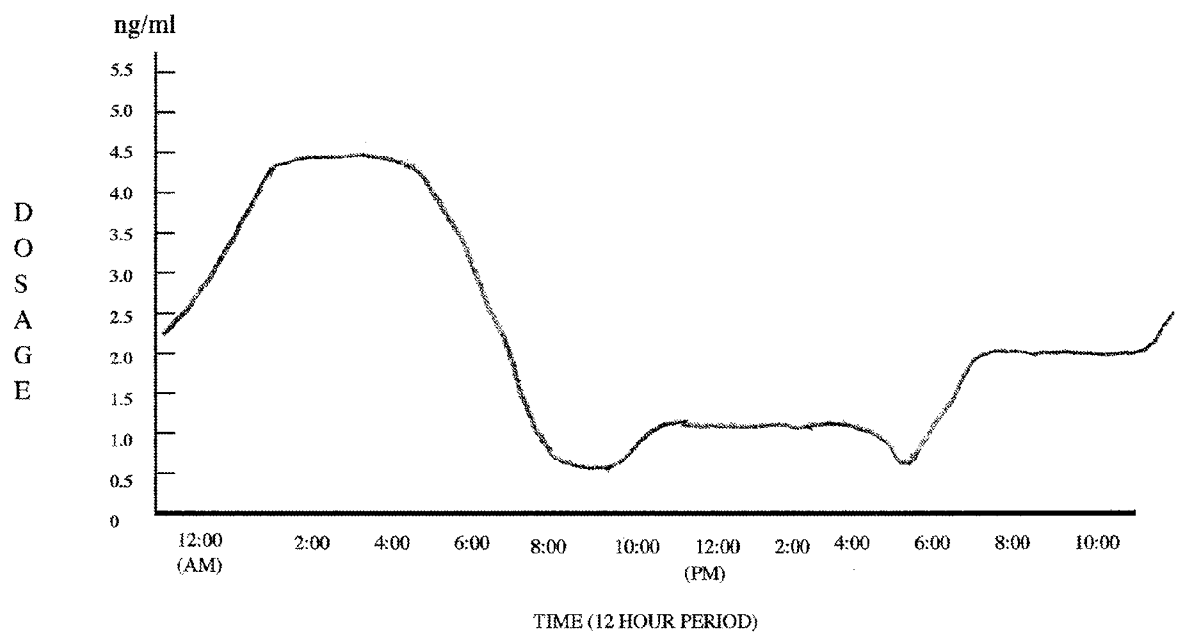
FIG. 17 illustrates an exemplary administration profile for an oxybutynin delivery system tailored to urinary incontinence.

The time/dose chart should appear as shown in FIG. 17

Applications

Headache and Migraine

Example

Zolmitriptan

An automated, and programmed, pulsatile drug delivery regimen is desired to in order to increase drug concentrations automaticaly in the evening to provide needed medication, in the very early morning (0200-0400) while asleep, and again later on (0800-1000) upon waking. Then, during the daytime work hours, decrease concentrations to allow for normal activities.

Chronotherapeutic Rationale:

Migraine, cluster and tension-type headaches may produce a headache that awakens an individual in the early morning hours (usually between 2 and 4 AM), or is present upon awakening. Those individuals with chronic tension-type headache are most likely to be awakened in the early morning hours due to headache. This headache also tends to be at its worst severity at that time of day. A variety of causes may account for this early-morning pattern to the headaches.

Additionally, primary headaches associated with late sleeping or weekends are caused by caffeine withdrawal. Sleeping in late delays morning caffeine intake, which often leads to withdrawal and migraine. Many people reduce their caffeine intake on weekends, which readily explains the weekend increase in migraine attacks. Fewer migraines occur on Mondays and Tuesdays than on other days of the week.

Medications for headache and migraine include:

Abortive Medications

Analgesics with caffeine such as Excedrin® Migraine (acetaminophen, aspirin and caffeine).

Analgesics with caffeine and barbiturates such as Fiorinal® (butalbital, aspirin and caffeine) and Fioricet® (butalbital, acetaminophen and caffeine).

Non steroidal antiinflammatory drugs (NSAIDs) such as Advil® (ibuprofen), and Aleve® (naproxen sodium).

Ergotamines such as Cafergot® (caffeine and ergotamine tartrate) and Migranal® (dihydroergotamine).

Triptans such as Zomig® (zolmitriptan), Maxalt® (rizatriptan), Imitrex® (sumatriptan), Frova® (frovatriptan), Axert® (almotriptan) and Amerge® (naratriptan).

Excedrin Migraine is a registered trademark of Bristol-Myers Squibb Company

Fiorinal and Fioricet are registered trademarks of Novartis Pharmaceuticals Corporation Advil is a registered trademark of Whitehall-Robbins Healthcare Aleve is a registered trademark of Bayer Corporation Cafergot and Migranal are registered trademarks of Novartis Pharmaceuticals Corporation Zomig is a registered trademark of AstraZeneca Maxalt is a registered trademark of Merck & Co., Inc.

Imitrex is a registered trademark of GlaxoSmithKline

Frova is a registered trademark of Elan Pharmaceuticals/UCB Pharma, Inc.

Axert is a registered trademark of Pharmacia

Amerge is a registered trademark of GlaxoSmithKline

Preventive Medications

Beta blockers such as Inderal® (propranolol)*, Blocadren® (timolol maleate)*, and metoprolol.

Calcium-channel blockers such as Cardizem® (diltiazem) and Procardia® (nifedipine).

Antidepressants such as Prozac® (fluoxetine), Paxil® (paroxetine) and Zoloft® (sertraline).

Anticonvulsants such as Depakote® (valproic acid or divalproex sodium).

NSAIDs such as Orudis® (ketoprofen) and Aleve® (naproxen sodium).

Inderal is a registered trademark of AstraZeneca

Blocadren is a registered trademark of Merck & Co, Inc.

Cardizem is a registered trademark of Aventis Pharmaceuticals

Procardia is a registered trademark of Pfizer Inc.

Prozac is a registered trademark of Eli Lilly and Company

Paxil is a registered trademark of GlaxoSmithKline

Zoloft is a registered trademark of Pfizer Inc.

Depakote is a registered trademark of Abbott Laboratories

Orudis is a registered trademark of Aventis Pharmaceuticals

Aleve is a registered trademark of Bayer Corporation

Example

Zolmitriptan

Blood plasma concentration between 1.0 and 5.0 ng/ml. Theoretical unenhanced transdermal flux for zolmitriptan (Berner-Cooper predictive model) is 6.02 ug/cm$^2$/hr. Thus, dosing could be optimized using the ChronoDose system. For example, pulsatile delivery should have blood plasma concentrations (BPC) as set forth below within the following ranges at the following times:

Peak 1 (Highest)

2:00 am-4:00 am: BPC should be in the highest therapeutic range of between 3.5-4.0 ng/ml.

Peak 2 (Highest)

8:00 am-10:00 am: BPC should be in the highest therapeutic range of between 3.5-4.0 ng/ml.

Trough (Lowest)

12:00 pm to 12:00 am: BPC should be in the lowest therapeutic range of between 1.0-3.0 ng/ml.

Figure 18:
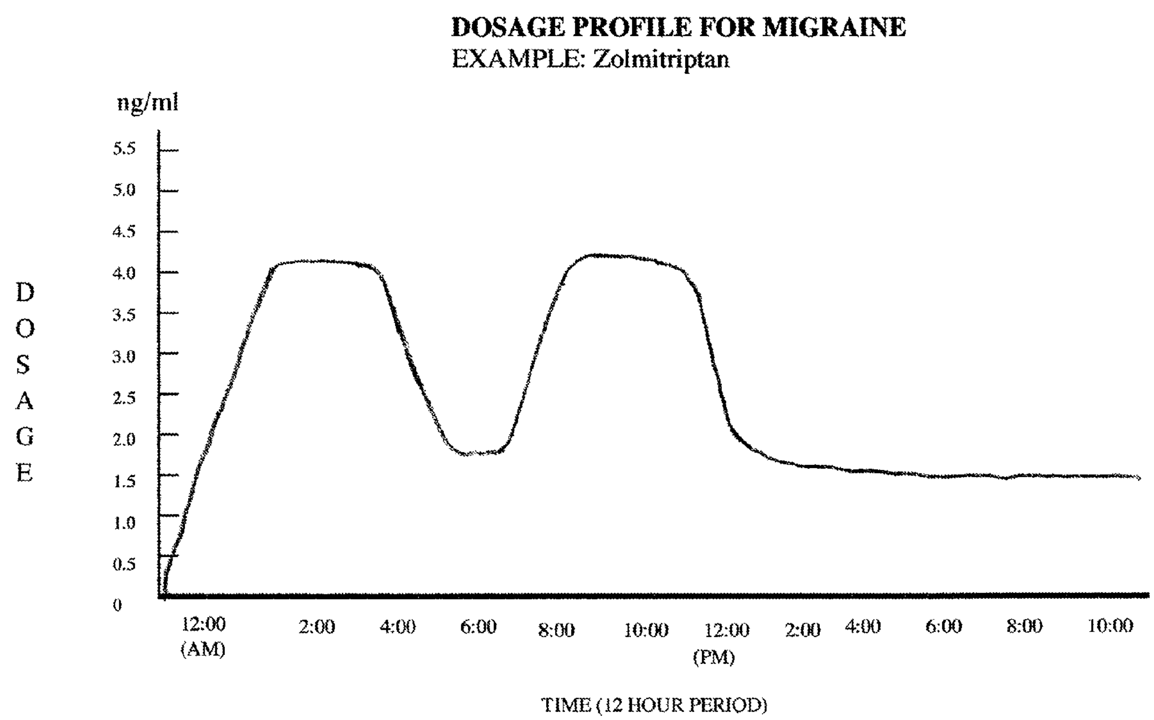
FIG. 18 illustrates an exemplary administration profile for a zolmitriptan delivery system tailored to treat migraine.

The time/dose chart should appear as shown in FIG. 18

Applications

Diabetes

Example

Miglitol

An automated, and programmed, pulsatile drug delivery regimen is desired to in order to increase drug concentrations automaticaly in the morning (0800), midday (1200) and evening (1800) which coincide with mealtimes.

Miglitol is indicated as an adjunct to diet to improve glycemic control in patients with non-insulin-dependent diabetes mellitus (NIDDM) whose hyperglycemia cannot be managed with diet alone.

Theoretical unenhanced transdermal flux for miglitol (Berner-Cooper predictive model) is 49.24 ug/cm$^2$/hr.

Thus, dosing could be optimized using the ChronoDose system. For example, pulsatile delivery should have blood plasma concentrations (BPC) as set forth below within the following ranges at the following times:

Peak 1 (Highest)

8:00 am-10:00 am: BPC should be in the highest therapeutic range.

Peak 2 (Highest)

12:00 am-2:00 pm: BPC should be in the highest therapeutic range.

Trough (Highest)

6:00 pm to 8:00 am: BPC should be in the lowest therapeutic range.

Figure 19:
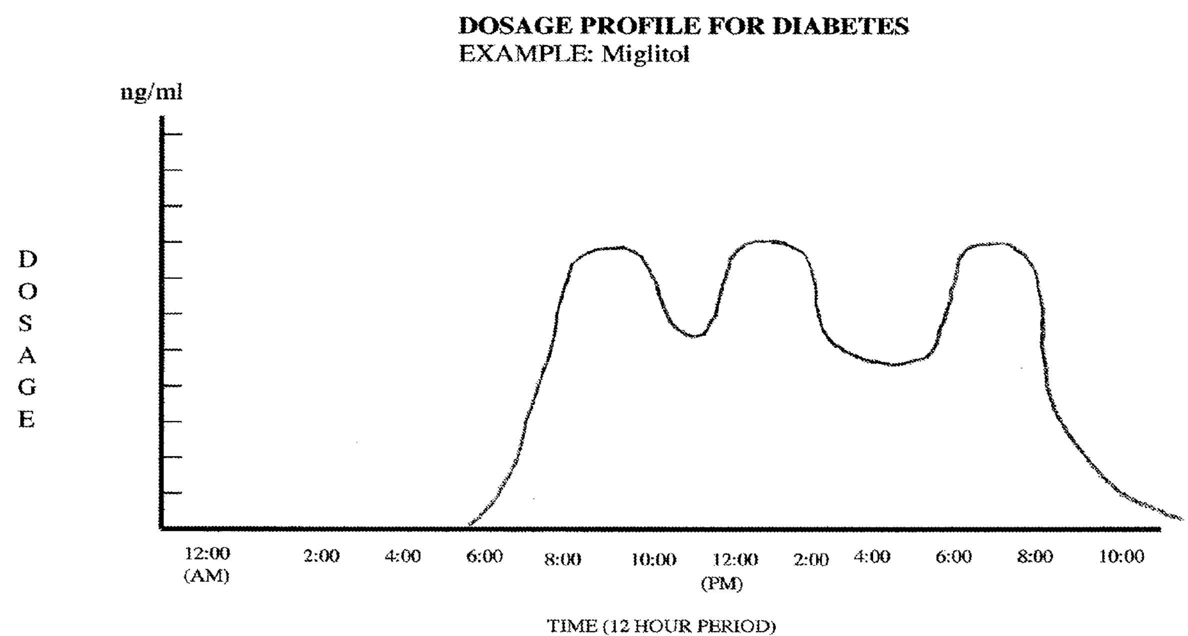
FIG. 19 illustrates an exemplary administration profile for a miglitol delivery system tailored to treat diabetes.

The time/dose chart should appear as shown in FIG. 19

Applications

Pain Management

Example

Fentanyl

Many diseases and pain-causing situations (post-surgery, post trauma) have predictable pain patterns. For example, cortisol is virtually absent in the body overnight, and this is what fights inflammation. Thus, any pain resulting from inflammation (rheumatoid arthritis, post-surgical pain, post-traumatic pain, back pain, neurological pain) is most common in the early morning hours between 3:00 a.m. and 8:00 a.m. Migraine pain is worst around 6:00 a.m. Ankylosing spondylitis pain surges between 6:00 a.m. and 9:00 a.m. Osteoarthritis pain surges in mid-afternoon.

Pain varies tremendously from one patient to the next, and there are also some studies suggesting that the intensity of pain varies according to time of day. In human studies, pain induced experimentally was reported to be maximal in the morning, or in the afternoon or at night. A circadian pattern of pain has been seen in patients suffering from pain produced by different diseases. For instance, highest toothache intensity occurred in the morning, while biliary colic, migraine, and intractable pain were highest at night. Patients with rheumatoid anhritis reported peak pain early in the morning, while those with osteoarthritis of the knee indicated that the maximal pain occurred at the end of the day. The effectiveness of opioids appears also to vary according to time of day, but large differences in the time of peak and low effects were found. Peak pain intensity and narcotic demands occur early in the morning, or it can be at the end of the day. Pain is a complex phenomenon and specific to each clinical situation.

An automated, and programmed, pulsatile transdermal drug delivery regimen is needed to substantially increase blood plasma concentrations of Fentanyl or other pain medications, automatically between 3:00 am and 8:00 am, while people sleep, where pain results from inflammation, because cortisone, a key inflammation fighter, is lowest in the body at that time. Additionally, an automated, and programmed, pulsatile transdermal drug delivery regimen is needed to substantially increase blood plasma concentrations of Fentanyl or other pain medications automatically between 6:00 am and 9:00 am for Ankylosing spondylitis pain, and in mid-afternoon for Osteoarthritis pain.

Other pain medication includes: codeine, dihydrocodeine, hydrocodone or hydromorphone, Sufentanil, Nalbuphine, Buprenorphine, Hydromorphone and any type of opiate derivative.

These are exemplary choices for transdermal pain management since they are effective, there is considerable hepatic first pass effect and a short half life, and they are skin permeable.

For example, for pain that increases with inflammation, as in the situations noted above, our regimen would suggest automated and programmed, transdermal pulsatile delivery of fentanyl to reach blood plasma concentrations (BPC) as set forth below within the following ranges at the following times:

Peak 1 (Highest)

3:00 am-8:00 am: BPC of fentanyl should be in the highest therapeutic range of between 2-8 ng/ml.

Peak 2 (Lowest)

8:00 am-5:00 pm: BPC should be in a moderate therapeutic range of between 1-3 ng/m.

Peak 3 (Middle)

5:00 pm to 3:00 am: BPC should be in the lowest therapeutic range of between 2-5 g/ml.

Figure 20:
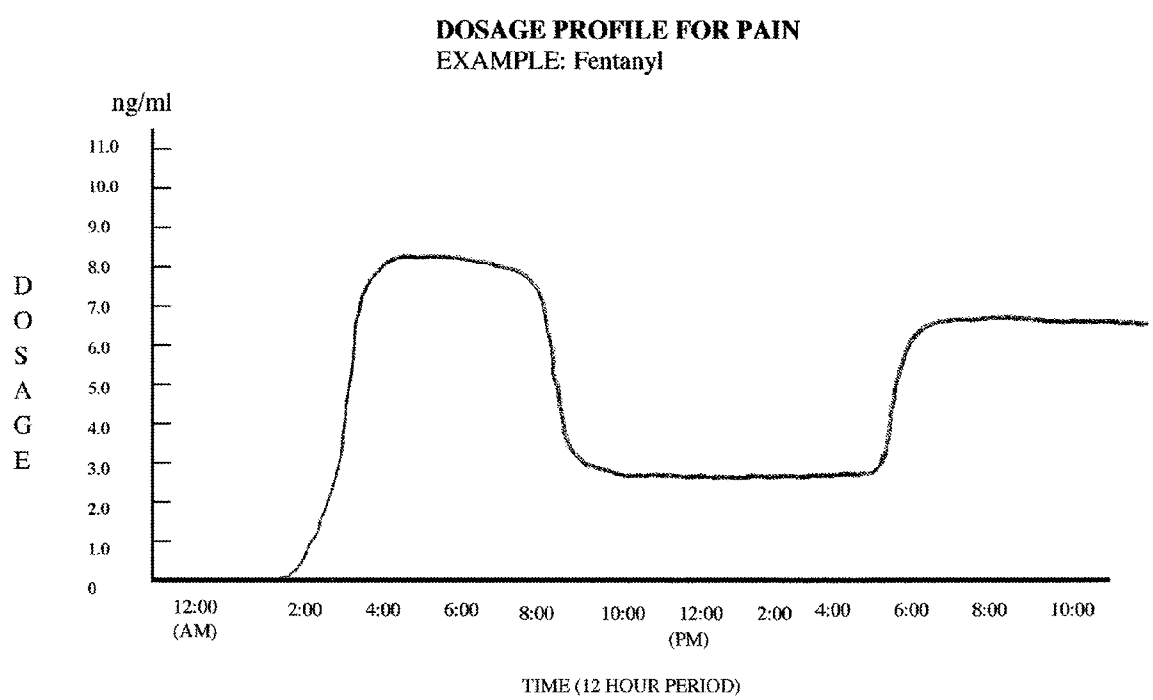
FIG. 20 illustrates an exemplary administration profile for a fentanyl delivery system tailored to treat pain.

The time/dose chart should appear as shown in FIG. 20

Applications

Cancer

Example

Cancer chronotherapy is attracting attention as a novel and logical therapy in which anti-cancer drugs are administered with optimal timing according to circadian rhythms of anti-cancer action and those of adverse effects on normal cells. Advances in chronobiology have identified the suprachiasmatic nucleus (SCN) as the center of biological rhythms and the area in which clock genes such as PER1, PER2, PER3, CLOCK, BMAL1, TIM, CRY1, CRY2, tau act to generate and coordinate biological rhythms. These findings have led to the development of chronotherapy. Clinically, patients with advanced gastrointestinal cancer have been treated by chrono-modulated chemotherapy with good response. For colorectal cancer patients with un resectable liver metastases, chronotherapy with g-OHP+5-FU+FA (folinic acid) has been reported to allow complete surgical resection of liver metastases, resulting in 39-50% 5-year survival.

The circadian timing of surgery, anticancer drugs, radiation therapy, and biologic agents can result in improved toxicity profiles, tumor control, and host survival. Optimally timed cancer chemotherapy with doxorubicin or pirarubicin (06:00 h) and cisplatin (18:00 h) enhanced the control of advanced ovarian cancer while minimizing side effects, and increased the response rate in metastatic endometrial cancer. Therapy of metastatic bladder cancer with doxorubicin-cisplatin was made more tolerable by this same circadian approach resulting in a 57% objective response rate. This optimally timed therapy is also effective in the adjuvant setting, decreasing the expected frequency of metastasis from locally advanced bladder cancer. Circadian fluorodeoxyuridine (FUDR) continuous infusion (70% of the daily dose given between 15:00 h and 21:00 h) has been shown effective for metastatic renal cell carcinoma resulting in 29% objective response and stable disease of more than 1 yr duration in the majority of patients. Toxicity is reduced markedly when FUDR infusion is modulated to circadian rhythms Chronotherapy has also been used to lower the amount of side effects from chemotherapy drugs. Over the years, doctors have realized that by giving two of these drugs, Adriamycin and cisplatin, in the morning and evening, respectively, side effects could be cut in half.

Thus, dosing could be optimized using the ChronoDose system. For example, pulsatile delivery should have blood plasma concentrations (BPC) as set forth for each specific medication.

Figure 21A:
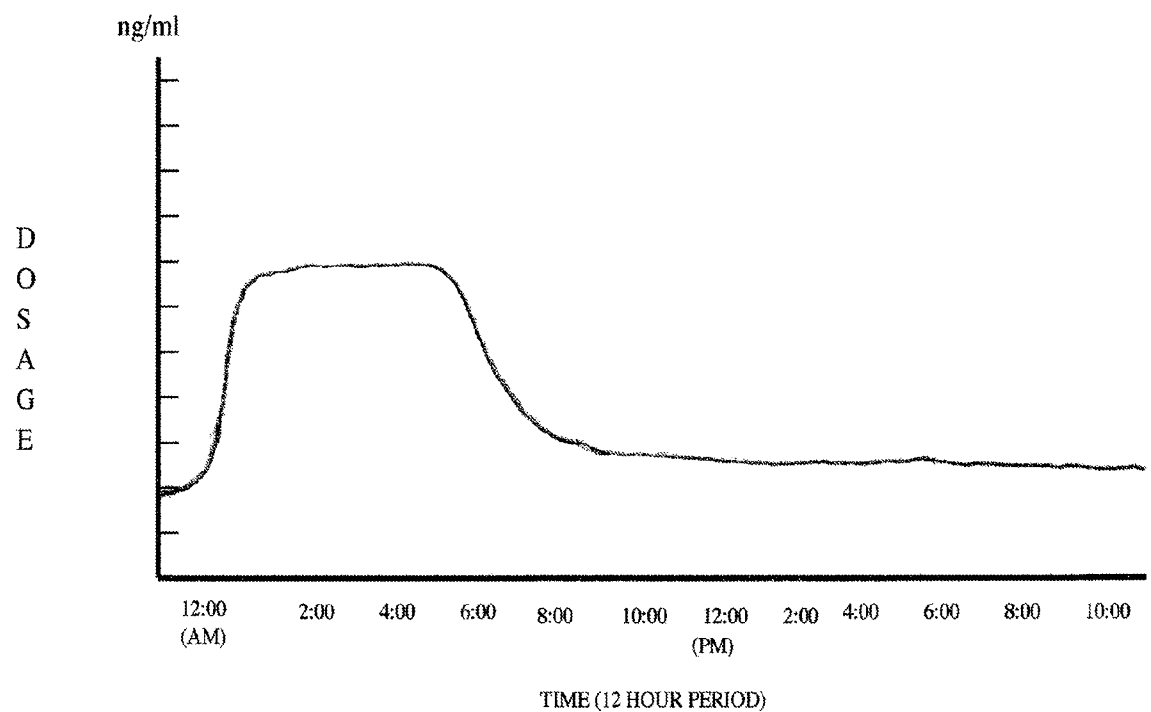
FIGS. 21A-C illustrates an exemplary administration profile for 5-fluorouracil, doxorubicin and cisplatin delivery system tailored to treat cancer.
Figure 21B:
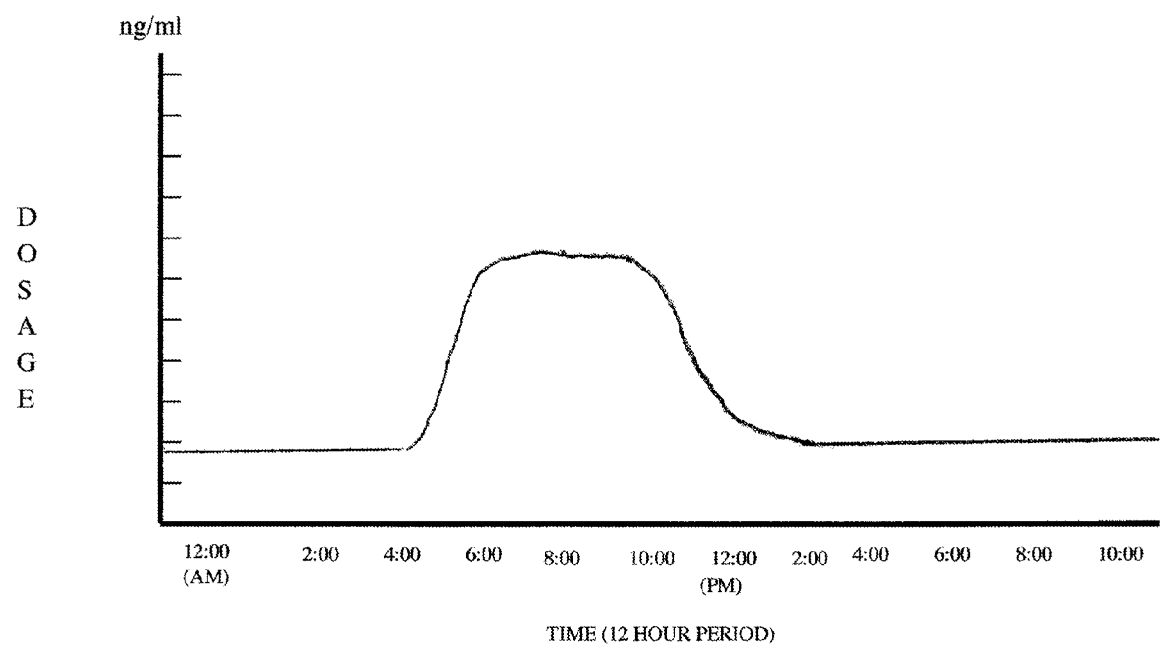
Figure 21C:
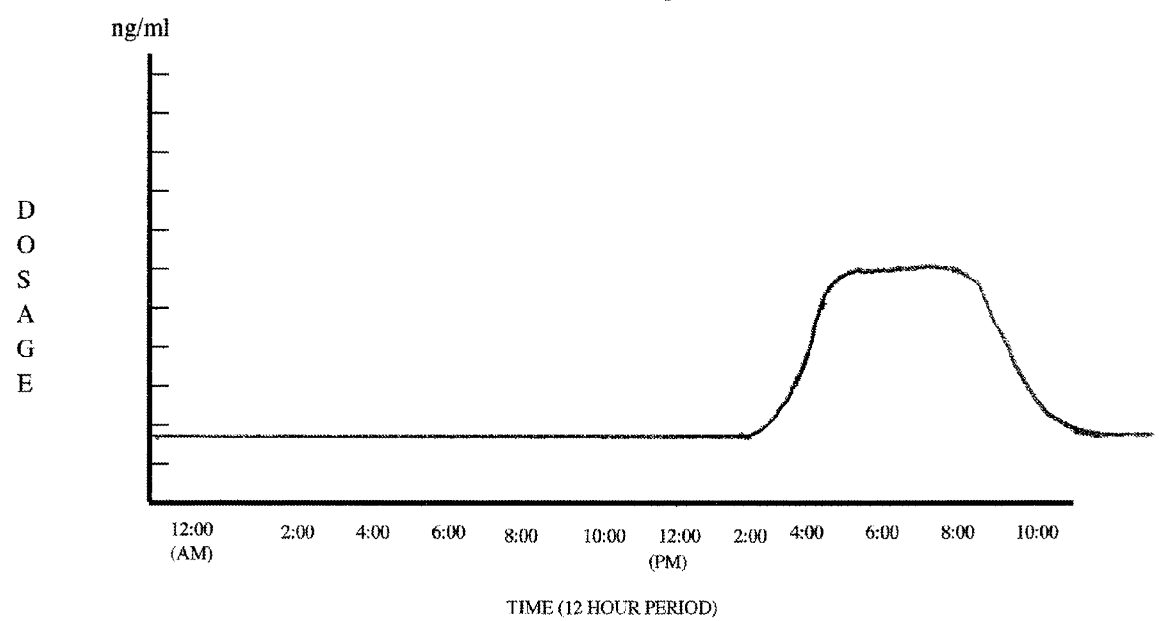

The time/dose charts should appear as shown in FIG. 21 (a, b & c)

Applications

Acquired Immune Deficiency Syndrome (AIDS/HIV)

Examples

Zidovudine, Didanosine

Currently available antiretroviral drug regimens are able to suppress HIV replication and allow CD4 recovery in the vast majority of patients with HIV infection. The challenge is to match each patient to the regimen that is most likely to durably suppress HIV replication enough to prevent resistance selection without causing treatment-limiting toxicities. It is also critical, but difficult, to know when to begin treatment relative to CD4 cell count and plasma viral load.

Adherence to antiretroviral therapy for the treatment of HIV infection and AIDS has become one of the most important clinical challenges among HIV health care providers and patients. Adherence to the prescribed regimen may predict which patients achieve undetectable viral loads. Unfortunately, non-adherence is common in antiretroviral therapy and has been associated with increases in viral load and the development of drug resistance. Efforts to maximize patient adherence are critical for suppressing HIV replication and preventing the transmission of drug-resistant virus.

Automated and programmed, transdermal pulsatile delivery of zidovudine to reach blood plasma concentrations (BPC) as set forth below within the following ranges at the following times:

Peak 1 (Highest)

5:00 am-9:00 am: BPC of zidovudine should be in the highest therapeutic range.

Peak 2 (Highest)

7:00 pm to 11:00 pm: BPC should be in the highestest therapeutic range.

Theoretical unenhanced transdermal flux for zidovudine (Berner-Cooper predictive model) is 17.94 ug/cm$^2$/hr.

Figure 22:
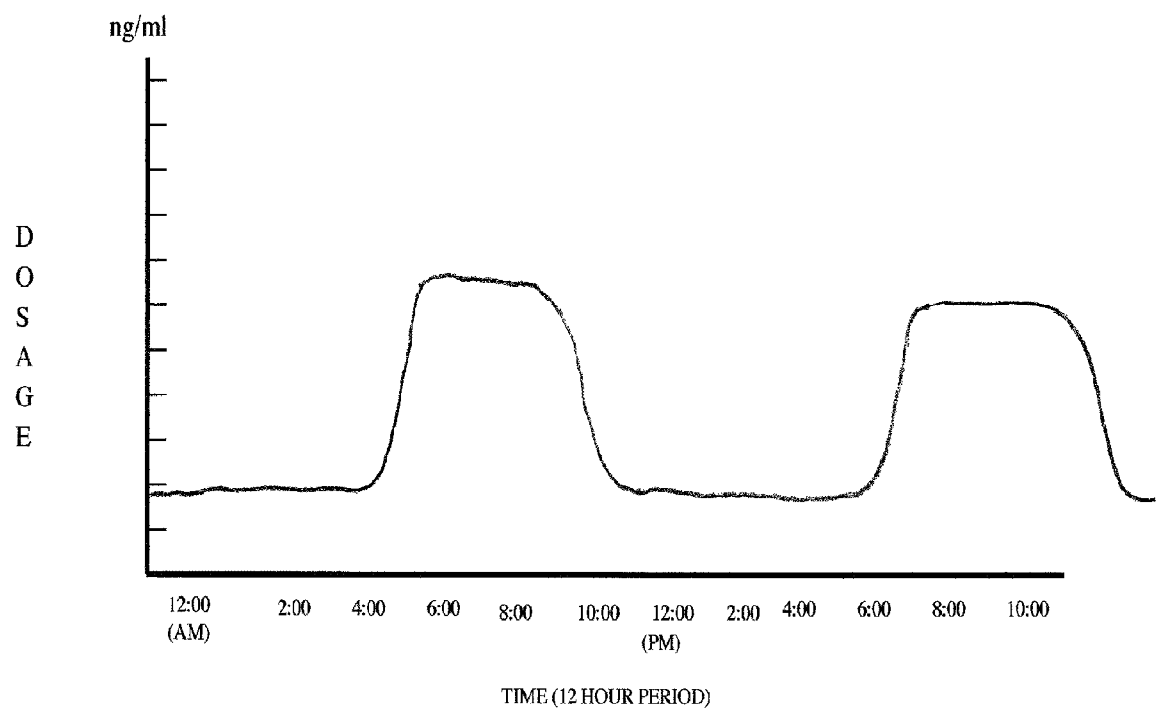
FIG. 22 illustrates an exemplary administration profile for a zidovudine delivery system tailored to treat AIDS.

The time/dose chart should appear as shown in FIG. 22

Applications

Epilepsy

Example

Gabapentan

In the majority of persons with the brain disorder epilepsy, seizures recur at predictable times of day. About half of those with epilepsy experience seizures mainly in waking hours. About one-quarter have them mainly in sleep. In the others, timing is less consistent; their seizures strike both day and night.

More than twenty anti-seizure medications (also called anticonvulsant or anti-epilepsy drugs) currently are available in the United States. Some are specifically designed not to interfere with the activity of other drugs, including birth control pills. They include gabapentin (Neurontin), lamotrigine (Lamictal), topiramate (Topamax), tiagabine (Gabatril), levetiracetam (Keppra), and oxcarbazepine (Trileptal).

None of the newer medications and only two of the older ones, valproate and phenyloin, have been studied with regard to how they work when taken at different times of the day or in different phases of the menstrual cycle. Whether the findings in valproate and phenyloin can be generalized to other anti-epilepsy drugs is not known; the results do raise issues, however, that urgently need further study. Studies of valproate show that people absorb it more slowly and less efficiently when they take it in the evening than in the morning. This finding is of concern because protection against seizures usually is needed most in NREM sleep, the state that dominates the first half of a night's sleep.

Automated and programmed, transdermal pulsatile delivery of gabapentan to reach blood plasma concentrations (BPC) as set forth below within the following ranges at the following times:

Peak 1 (Highest)

5:00 am-9:00 am: BPC of gabapentan should be in the highest therapeutic range.

Peak 2 (Highest)

7:00 pm to 11:00 pm: BPC should be in the highestest therapeutic range.

Figure 23:
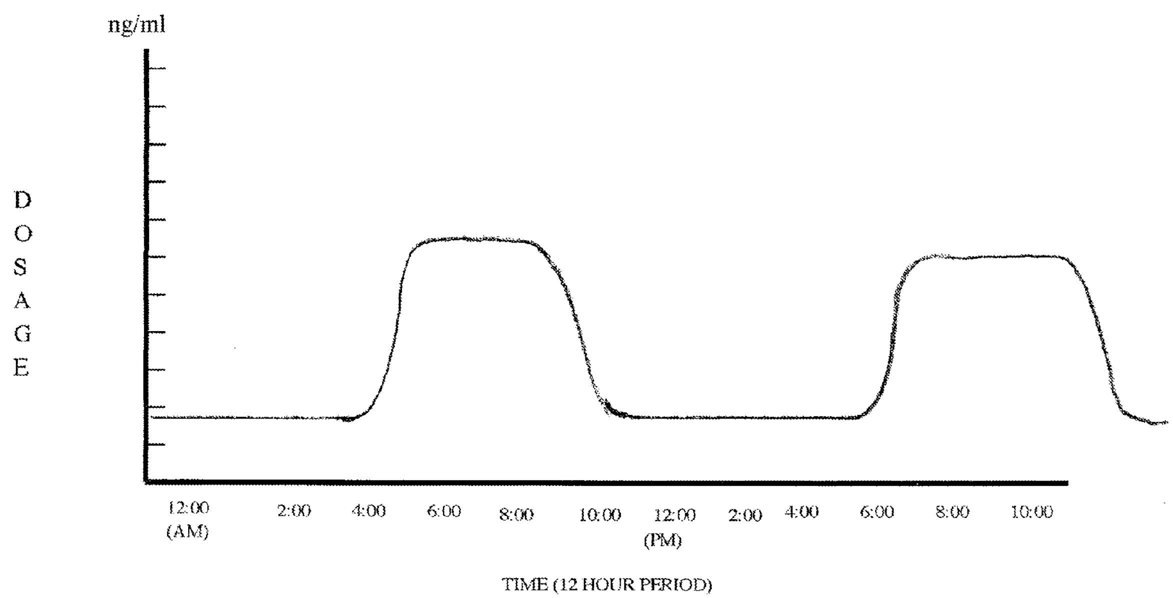
FIG. 23 illustrates an exemplary administration profile for a gabapentin delivery system tailored to epilepsy.

The time/dose chart should appear as shown in FIG. 23

Applications

Cold and Flu Treatment

Example

Triprolidine

Cold and flu symptoms are worst from midnight until the early morning because the concentration of cortisol is lowest at that time. Current nighttime cold and flu medication end up losing efficacy by early morning when cold and flu symptoms are highest. Therefore people suffering from a cold or flu are often unpleasantly awoken by an increase in symptoms, cutting sleep short. Set and put on before bedtime, the present invention will automatically deliver a larger dose of medication and immuno-boosters in the early morning hours to more effectively combat the peak cold and flu symptoms that occur in the morning.

This implementation uses prescription or OTC cold medicine alone or optionally in combination with certain transdermally efficacious vitamins and immune system boosters to provide a total solution to cold and flu ailments. This is the first cold therapy that combines OTC medicine with supplemental immuno-boosters in a comprehensive and automated manner.

In a particular application, the Cold and Flu automated transdermal drug delivery system utilizes OTC cold medicine, Vitamin C, Echinacea, and Zinc to provide a total solution to cold and flu ailments, and all while a person sleeps. The Cold/Flu system releases these combination of compounds every 2 hours throughout the night, with a higher dosage of compounds being released in the morning to combat these proven middle of the night and early morning symptoms, which are the worst of the day. Users will experience less severe cold and flu symptoms during the morning hours, will not have their sleep cycle cut short, and will wake up feeling symptom-free.

Figure 24:
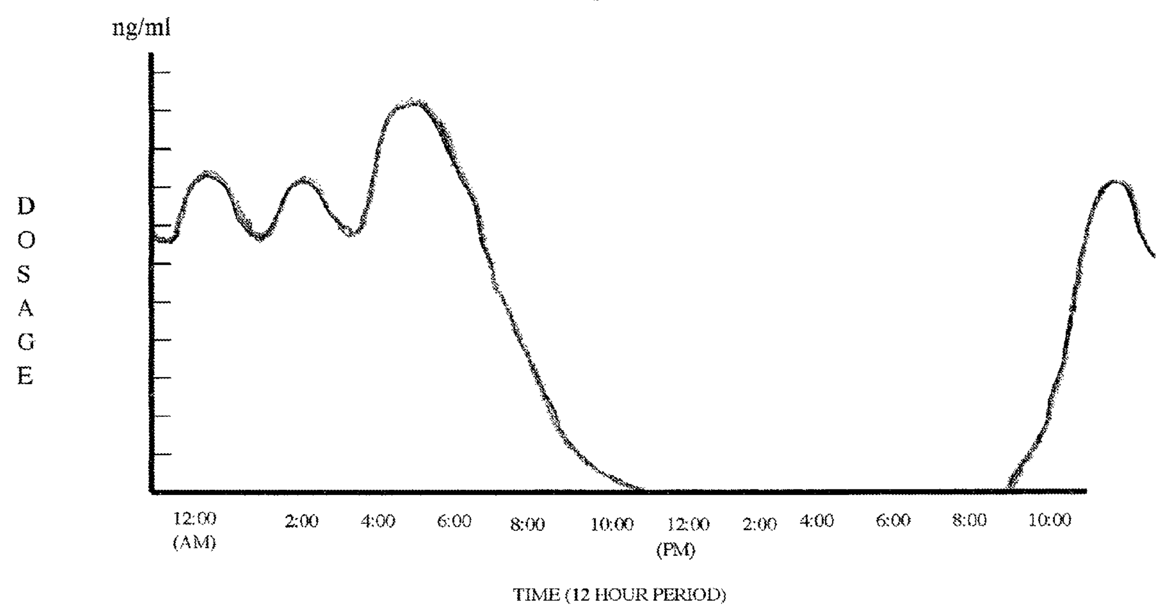
FIG. 24 illustrates an exemplary administration profile for a triprolidine delivery system tailored to treat colds and flu.

The time/dose chart should appear as shown in FIG. 24.

Applications

Weight Control, Vitamin and Herbal Supplementation

In yet another application, a series of weight loss vitamins and supplements is administered in small distinct doses many times over several days. Vitamins and supplements are absorbed by the body in small dosages. Contrary to popular belief, once-a-day products are not maximally effective because excess dosages are excreted unused. This implementation of the present invention precisely controls the timing and dosage of small but distinct amounts of vitamins and supplements during a 24-hour period to ensure that vitamins and supplements are constantly bio-available for optimal absorption and cellular function. Greater doses are automatically released prior to mealtimes to counter appetite cravings, resulting in a much more effective diet program.

Applications

In General

The present invention is particularly useful in applications in which it is necessary and/or desirable to start the administration of a drug, stop the administration of a drug, and/or increase/decrease the dosage of a drug at a time when it is inconvenient or impossible for a patient to initiate the necessary actions. This is particularly useful for a wide variety of drug administration applications that benefit when an administration is started, stopped, or changed while a person is sleeping. As research and knowledge of chronotherapy increases, it is contemplated that a wide variety of applications will be discovered in which benefit is realized by starting, stopping and/or changing the drug administration while a patient sleeps.

In each of the examples, treatment is continued as needed to provide superior symptomatic relief, prevent exacerbation of symptoms, and/or prevent and/or delay progression of the disease state or condition in the patient, or until it is no longer well tolerated by the patient, or until a physician terminates treatment. For example, a physician may monitor one or more symptoms and/or serum levels of active material and/or metabolic by-product(s) in a patient being treated according to this invention and, upon observing attenuation of one or more symptoms for a period of time, conclude that the patient can sustain the positive effects of the above-described treatment without further administration for a period of time. When necessary, the patient may then return at a later point in time for additional treatment as needed.

As used herein, 'day' means a 24-hour period. Thus, for example, 'for at least three consecutive days' means for at least a 72-hour period. During or after the treatment, a physician may monitor one or more symptoms and/or serum levels in the patient and, upon observing an improvement in one or more of the parameters for a period of time, conclude that the patient can sustain the positive effects of the treatment without further administration of the active material for a period of time.

In order to use an active material for therapeutic treatment (including prophylactic treatment) of mammals including humans according to the methods of this invention, the active material is normally formulated in accordance with standard pharmaceutical practice as a pharmaceutical composition. According to this aspect of the invention there is provided a pharmaceutical composition comprising an active material in association with a pharmaceutically acceptable diluting substance or carrier, wherein the active material is present in an amount for effective treating or preventing a particular condition.

While individual needs may vary, determination of optimal ranges for effective amounts of an active ingredient (alone or in combination with other drugs) within the ranges disclosed herein is within the expertise of those skilled in the art. Accordingly, 'effective amounts' of each component for purposes herein are determined by such considerations and are amounts that improve one or more active ingredient functions and/or ameliorate on or more deleterious conditions in patients and/or improve the quality of life in patients.

Pharmaceutical Kits

The present invention also provides pharmaceutical kits for treating a particular symptom, condition and/or disease and/or improving a particular biological function, comprising one or more containers comprising one or more active compositions in accordance with this invention. Such kits can also include additional drugs or therapeutics for co-use with the active composition for treatment or prevention of a particular symptom, condition and/or disease and/or improving a particular biological function. In this embodiment, the active composition and the drug can be formulated in admixture in one container, or can be contained in separate containers for simultaneous or separate administration. The kit can further comprise a device(s) for ad-ministering the compounds and/or compositions, such as device 100 shown in FIG. 1, and written instructions in a form prescribed by a governmental agency regulating the manufacture, use or sale of pharmaceuticals or biological products, which instructions can also reflect approval by the agency of manufacture, use or sale for human administration.

Although the invention has been described and illustrated with a certain degree of particularity, it is understood that the present disclosure has been made only by way of example, and that numerous changes in the dosages, administration profiles, timing, as well as the combination and arrangement of parts can be resorted to by those skilled in the art without departing from the spirit and scope of the invention, as hereinafter claimed.

What is claimed is:

1. A method for delivering a bioactive agent to a human or animal comprising:

(a) providing a transdermal drug delivery device coupled to the human or animal, the transdermal drug delivery device comprising:

(i) a drug reservoir comprising the bioactive agent, (ii) a membrane in contact with the skin of the human or animal;

(iii) an electronic programmable timing mechanism;

(iv) a mechanism for causing the bioactive agent to be delivered from the drug reservoir to the membrane in response to the timing mechanism, the bioactive agent being delivered transdermally by passive diffusion from the membrane into the skin of the human or animal; and (v) an expandable waste reservoir for controlled discontinuance of the delivery of the bioactive agent;

(b) providing timing routines implemented by the timing mechanism, wherein the timing routines are selected to deliver the bioactive agent at a time, rate, sequence and/or cycle that is synchronized with a biological rhythm of the human or animal;

(c) delivering the bioactive agent from the drug reservoir to the membrane in response to the timing mechanism;

(d) transdermally delivering the bioactive agent from the membrane into the skin of the human or animal by passive diffusion; and (e) removing the bioactive agent and/or a carrier solution from the membrane via the expandable waste reservoir to discontinue delivery of the bioactive agent to the human or animal;

wherein the device is maintained in contact with the skin during removal of the bioactive agent and/or carrier solution via the expandable waste reservoir.

2. The method of claim 1 wherein the bioactive agent comprises a stimulant and the timing routines are selected to deliver the stimulant immediately before the human or animal wakes up.

3. The method of claim 1 wherein the bioactive agent comprises nicotine and the timing routines are selected to deliver the nicotine at times that are associated with nicotine cravings.

4. The method of claim 3 wherein at least one of the selected times corresponds to a time at which the human or animal experiences a morning nicotine craving.

5. The method of claim 1 wherein the bioactive agent comprises an antihistamine and the timing routines are selected to deliver the antihistamine while the human or animal sleeps.

6. The method of claim 1 wherein the time routines are selected to deliver the bioactive agent immediately before the human or animal wakes up.

7. A method for delivering a drug to a human or animal comprising:

(a) providing a transdermal drug delivery device comprising;

(i) a source of the drug;

(ii) a membrane in contact with the skin of the human or animal;

(iii) an electronic programmable timing mechanism;

(iv) a mechanism for causing the drug to be delivered from the source to the membrane in response to the timing mechanism, the drug being delivered transdermally by passive diffusion from the membrane into the skin of the human or animal;

(v) a solvent removal system comprising an expandable waste reservoir for removing carrier solution and/or remaining drug;

(b) providing timing routines implemented by the timing mechanism, wherein the timing routines are selected to deliver the drug at a time when the human or animal is expected to be asleep;

(c) delivering the drug from the source to the membrane in response to the timing mechanism;

(d) transdermally delivering the drug from the membrane into the skin of the human or animal by passive diffusion; and (e) removing carrier solution and/or remaining drug from the membrane via the expandable waste reservoir to discontinue delivery of the drug to the human or animal; and wherein the device is maintained in contact with the skin during removal of the carrier solution and/or remaining drug via the expandable waste reservoir.

8. The method of claim 7 wherein the timing routines terminate drug delivery at a time when the human or animal is expected to be asleep.

9. The method of claim 7 wherein the time routines increase the dosage of drug delivered at a time when the human or animal is expected to be asleep.

10. The method of claim 7 wherein the timing routines decrease the dosage of drug delivered at a time when the human or animal is expected to be asleep.

11. The method of claim 3 wherein the timing routine results in a plurality of nicotine delivery pulses with a most sustained pulse beginning during a one-hour period prior to waking in the morning.

12. The method of claim 3 wherein the timing routines include a cessation of nicotine dosage from after midnight to during a one-hour period prior to the time the human or animal wakes in the morning.

13. The method of claim 12 wherein the timing routines further include pulses associated with waking up and mid-day and evening meals.

14. The method of claim 3 wherein the timing routines include at least five preprogrammed pulses during the course of 24 hours.

15. The method of claim 3 wherein amplitudes of preprogrammed pulses in the afternoon are less than amplitudes of a first preprogrammed pulse in the morning and a preprogrammed pulse in the evening.

16. The method of claim 1 wherein the timing routines schedule no delivery of the bioactive agent in a time period from after midnight to 1 hour before waking in the morning and schedule a first delivery of the bioactive agent in the morning in a pulse which has an initial peak at from 1 to 4 hours after waking and a pulse peak width of from 1-6 hours.

17. The method of claim 1 wherein the bioactive agent and/or carrier solution is removed from the membrane via evaporation into the expandable waste reservoir.

18. The method of claim 1 wherein the expandable waste reservoir comprises a hydrophilic substance.

* * * * *